(12) United States Patent
Chenard et al.

(10) Patent No.: US 6,323,208 B1
(45) Date of Patent: *Nov. 27, 2001

(54) ATROPISOMERS OF 2,3-DISUBSTITUTED-(5.6)-HETEROARYL FUSED-PYRIMIDIN-4-ONES

(75) Inventors: Bertrand L. Chenard, Waterford; Willard M. Welch, Jr., Mystic, both of CT (US)

(73) Assignee: Pfizer Inc, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/259,413

(22) Filed: Jul. 23, 1998

Related U.S. Application Data

(60) Provisional application No. 60/057,990, filed on Sep. 5, 1997.

(51) Int. Cl.$^7$ .................. C07D 491/04; A61K 31/505
(52) U.S. Cl. ............................. 514/258; 544/278
(58) Field of Search .................. 544/278; 514/258

(56) References Cited

U.S. PATENT DOCUMENTS

| | | | |
|---|---|---|---|
| 3,558,610 | 1/1971 | Breuer et al. | 260/240 |
| 5,124,331 | * 6/1992 | Arita et al. | 514/253 |
| 5,252,584 | 10/1993 | Carling et al. | 514/312 |
| 5,268,378 | 12/1993 | Baker et al. | 514/312 |
| 5,284,957 | 2/1994 | Huff | 548/112 |
| 5,426,106 | 6/1995 | Kulagowski et al. | 514/233.2 |
| 5,475,008 | 12/1995 | Carling et al. | 514/312 |
| 5,532,236 | 7/1996 | Jacobsen et al. | 514/228.5 |
| 5,559,125 | 9/1996 | Kulagowski et al. | 514/312 |

FOREIGN PATENT DOCUMENTS

| | | |
|---|---|---|
| 769844 | 1/1972 | (BE) . |
| 2114607 | 10/1972 | (DE) . |
| 0807633 | 11/1997 | (EP) . |
| 807633 | * 11/1997 | (EP) . |
| 2131843 | 11/1972 | (FR) . |
| WO9213535 | 8/1992 | (WO) . |
| WO9838173 | 9/1998 | (WO) . |
| WO9838187 | 9/1998 | (WO) . |

OTHER PUBLICATIONS

Kretzchmar: "Uber derivate des 4–Oxo–3,4–dihydro–'2, 3–d!pyrimidin" Die Pharmazie, vol. 35, No. 5/6, Jun. 1980, pp. 253–256, XP002087482.

Mannschreck A., et al, "The Enantiomers of Methaqualone and Their Unequal Anticonvulsive Activity", European Journal of Medicinal Chemistry, Chimica Therapeutica, vol. 19, No. 4, 1984, p. 381–383, XP002064151.

Boltze K.H., et al, "Substituierte Chinazolinone–(4) Als Hypmotica Und Antikonvulsiva", Arzneimittel Forschung, Drug Research, vol. 13, No. 8, Aug. 1963, pp. 688–701, XP002064150.

Physicians' Desk Reference, 53 Ed., 1999, pp. 2604–2607.

Jackson, C. E, and Bryan, W. W., Amyotrophic Lateral Sclerosis, vol. 18, No. 1, 1998, pp. 27–39.

Synthesis of Some New 2–Styryl–3–0–Tolyl–4–Quinazolone as compound of Antifungal Activity; J. Inst. Chemists (India); vol. 60, pp. 58; Mar. 1988; (Miss.) Malti Rawat.

Synthesis of Some Quinazolones; Indian J. Pharm. Sci., 1986, 48(5), pp. 133–136; Jun. 1985; Vijai K. Srivastava, et al.

Synthesis of Heterocyclic Compounds Incorporating 4–Aminostilbene; Indian J. of Chem., vol. 24B, pp. 1039–1042; Oct. 1985; Rajendra S. Varma, et al.

Synthesis and Hypotensive Activity of Trisubstituted Quinazolinones; Eur. J. Med. Chem.Chim. Ther., 1985–20, No. 1, pp. 95–96; A. Kumar, et al.

Synthesis and Antiinflammatory Activity of 2–Substituted–Phenethyl–3–Substituted–Phenyl–4(3H)–Quinazolinones; Indian J. of Chem., vol. 23B, pp. 592–594; Jun. 1984; Inder Pal Singh, et al.

Recent Progress in Excitatory Amino Acid Research; Annual Reports in Medicinal Chem.; Chapter 6, pp. 53–64; 1994; James A. Monn, et al.

Neuronal Cell Death and Strategies for Neuroprotection; Annual Reports in Medicinal Chem.; Chapter 2, pp. 13–22; 1994;Christopher F. Bigge, et al.

Substituierte Chinazolinone–(4) als Hypnotica und Antikonvulsiva; pp. 688–701; Von K.–H. Boltze, et al.

Synthesis of Some 4H–3,1–Benzoxazin–4–Ones and 4–Quinazolones and Their Reaction with Hydrazines; U.A.R.J. Chem., 14, No. 2, pp. 197–205; 1971; A. Sammour, et al.

Anticonvulsant and Monoamine Oxidase Inhibitory Properties of newer Chlorostrylquinazolones; Pharm. Research Communications, vol. 11, No. 7, pp. 623–633; 1979; R. S. Misra, et al.

Styrylquinazolones as Monoamine Oxidase Inhibitors; Pharm. Research Communications, vol. 9, No. 5, pp. 437–447; 1977 R. S. Misra et al.

Synthesis of Some Quinazolone Derivatives Structurally Related to Certain Sedatives, Hypnotics and Anticonvulsant Agents; Pharmazie 34, H. 11, 1979; A. K. El–Ansary, et al.

(List continued on next page.)

Primary Examiner—Richard L. Raymond
Assistant Examiner—Hong Liu
(74) Attorney, Agent, or Firm—Peter C. Richardson; Paul H. Ginsburg; Kristina L. Konstas

(57) ABSTRACT

The present invention relates to novel atropisomers of 2,3-disubstituted-(5,6)-heteroarylfused-pyrimidin-4-ones, pharmaceutical compositions containing such compounds the use of such compounds to treat neurodegenerative, psychotropic, and drug and alcohol induced central and peripheral nervous system disorders.

16 Claims, No Drawings

OTHER PUBLICATIONS

Correlation between Monoamine Oxidase Inhibitors and Anticonvulsants; J. of the National Medical Assoc., vol. 72, No. 10, pp. 953–955, 1980; Chundradhar Dwivedi, et al.

Synthesis of Some 4–Substituted Phenylmercaptoacetic Acids; Arch. Pharm. (Weinheim) vol. 314, pp. 97–103; 1981; Rajendra S. Varma, et al.

Synthesis of 2–Styryl–3,6,8–Trisubstituted Qinazolin 4(3H) Ones as Anti–inflammatory Agents; J. Chem. Soc. Pak.; vol. 3, No. 4, pp. 209–213, 1981; V. S. Misra, et al.

Antimicrobial Activity of 2,3–Disubstituted 4 (3H)–Quinazolone Derivatives; Indian Journal of Forestry; vol. 7 (2), pp. 151–153, 1984; S. K. Shukla, et al.

Synthesis of Certain 4 (3H) Quinazolones likely to Possess CNS Depressant and Antimalarial Activities; Egypt J. Pharm. Sci. vol. 29 No. 1–4, pp. 595–604, 1988; U. L. El Sabagh, et al.

Synthesis and Antifungal Activity of 2–(4–aryl–2–pyrazolin–3–yl)–3–aryl–4–(3H)–Quinazolinones; Indian J. Pharm. Sci., vol. 53 (6), pp. 229–232, 1991; A. Malla Reddy, et al.

Pyrido[3,2–d]pyrimidin–4(3H)–ones; p. 4240–4246; W. J. Irwin, et al.

Synthesis of Some Quinazolone Derivatives Structurally Related to Certain Sedatives, Hypnotics and Anticonvulant Agents; Dept. of Organic Chemistry; Pharmazie 34, H. vol. 11, 1979; A. K. El–Ansary, et al.

Seach for New Anthelmintics Part IV Synthesis of Phenoxy Acid–Salts of Piperazine Containing Quinazolone Moiety; Acta Ciencia Indica; vol. XVI, C, 3, 251, pp 755–763, 1990; S. S. Tiwari, et al.

4–(3H)–Quinazolones Part II: 2–Alkyl or Arylaminomethyl Substituted Cinnamyl–3–p–(N–Phenylthiouredo-sulfophenyl)4–(3H)–Quinazolones; J. Inst. Chemists (India), vol. 63, p. 66–69, Mar., 1991; V. B. Gaur, et al.

Structure activity relationships in the development of excitory amino acid receptor agonist and competitive antagonists; TiPS; vol. 11, pp. 25–33, 1990; Jeff C. Watkins, et al.

The non–NMDA antagonist, NBQX and GYKI 52466, protect against cortical and striatal cell loss following transient global ischaemia in the rat; Institute of Psychiatry; 571, pp 115–120, 1992; Eliane Le Peillet, et al.

2–3–Dihydroxy–6–nitro–7–sulfamoyl–benzo(F)quinoxaline: A Neuroprotectant for Cerebral Ischemia; Brain Research; vol. 247, pp. 571–574 1990; Malcolm J. Sheardown et al.

Modulation of N–methyl–D–aspartate receptor–mediated increases in cytosolic calcium in cultured rat cerebella granule cells; Brain Research ; 552, pp. 13–22, 1991; T. N. Parks, et al.

Delayed AMPA receptor blockade reduces cerebral infarction induced by focal ischemia; NeuroReport; vol. 2, No. 8, pp. 473–476, 1991; Alastair M. Buchan, et al.

(3SR,4aRS,6RS,8aRS)–6–[2–(1H–Tetrazol–5–yl)ethyl] decahydroisoquinoline–3–carboxylic Acid: A structurally Novel, Systemically Active, Competitive AMPA Receptor Antagonist; J. Med. Chem.; pp. 2046–2048, 1993; Paul L. Ornstein, et al.

New Developments in the Molecular Pharmacology of α–Amino–3–hydroxy–5–methyl–4–isoxazole Propionae and Kainate Receptors; Pharmacol. Ther. vol. 70, No. 1, p. 65–89, 1996; Elizabeth J. Fletcher et al.

ARICEPT® (Donepezil Hydrochloride tablets); US Product Prescribing Information; pp. 1–20, 1998; Pfizer Inc.

Rogawski, "Therapeutic potential of excitory amino acid antagonists: channel blockers and 2,3–benzodiazepines," TIPS, vol. 14, pp. 325–331, Sep. 1993.*

Bigge et al., "Agonists, Antagonists and Modulators of the N–methyl–D–aspartic acid (NMDA) and alpha–amino–3–hydroxy–5–methyl–4–isoxazolepropanoic acid (AMPA) Subtypes of Glutamate Receptors," Current Opinion in Therapeutic Patents, pp. 951–989, Jul. 1993.*

Chemical Abstract 77:5512t, vol. 77, No. 1, Jul. 1972.*

* cited by examiner

ATROPISOMERS OF 2,3-DISUBSTITUTED-(5,6)-HETEROARYL FUSED-PYRIMIDIN-4-ONES

This non-provisional application is based upon and claims priority from provisional Application Ser. No. 60/057,990 filed Sep. 5, 1997.

BACKGROUND OF THE INVENTION

The present invention relates to novel atropisomers of 2,3-disubstituted-(5,6)-heteroarylfused-pyrimidin-4-ones of the formula 1, as described below, their pharmaceutically acceptable salts, pharmaceutical compositions containing them and their use in treating neurodegenerative, psychotropic, and drug and alcohol induced central and peripheral nervous system disorders.

The role of excitatory amino acids, such as glutamic acid and aspartic acid, as the predominant mediators of excitatory synaptic transmission in the central nervous system has been well established. Watkins & Evans, *Ann. Rev. Pharmacol. Toxicol.*, 21, 165 (1981); Monaghan, Bridges,and Cotman, *Ann. Rev. Pharmacol. Toxicol.*, 29, 365 (1989); Watkins, Krogsgaard-Larsen, and Honore, *Trans. Pharm. Sci.*, 11, 25 (1990). These amino acids function in synaptic transmission primarily through excitatory amino acid receptors. These amino acids also participate in a variety of other physiological processes such as motor control, respiration, cardiovascular regulation, sensory perception, and cognition.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA). The second general type is the G-protein or second messenger-linked "metabotropic" excitatory amino acid receptor. This second type, when activated by the agonists quisqualate, ibotenate, or trans-1-aminocyclopentane-1,3-dicarboxylic acid, leads to enhanced phosphoinosoitide hydrolysis in the postsynaptic cell. Both types of receptors appear not only to mediate normal synaptic transmission along excitatory pathways, but also participate in the modification of synaptic connection during development and changes in the efficiency of synaptic transmission throughout life. Schoepp, Bockaert, and Sladeczek. *Trends in Pharmacol. Sci.*, 11, 508 (1990); McDonald and Johnson, Brain Research Reviews, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

Excitatory amino acid excitotoxicity has been implicated in the pathophysiology of a number of neurological disorders. This excitotoxicity has been implicated in the pathophysiology of acute and chronic neurodegenerative conditions including stroke, cerebral ischemia, spinal cord trauma, head trauma, Alzheimer's Disease, Huntington's Chorea, amyotrophic lateral sclerosis, epilepsy, AIDS-induced dementia, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, ocular damage and retinopathy, idiopathic and drug-induced Parkinson's Disease and cerebral deficits subsequent to cardiac bypass surgery and grafting. Other neurological conditions that are caused by glutamate dysfunction require neuromodulation. These other neurological conditions include muscular spasms, migraine headaches, urinary incontinence, psychosis, addiction withdrawal (such as alcoholism and drug addiction including opiate, cocaine and nicotine addiction), opiate tolerance, anxiety, emesis, brain edema, chronic and acute pain, convulsions, retinal neuropathy, tinnitus and tardive dyskinesia. The use of a neuroprotective agent, such as an AMPA receptor antagonist, is believed to be useful in treating these disorders and/or reducing the amount of neurological damage associated with these disorders. The excitatory amino acid receptor (EAA) antagonists are also believed to be useful as analgesic agents.

Several studies have shown that AMPA receptor antagonists are neuroprotective in focal and global ischemia models. The competitive AMPA receptor antagonist NBQX (2,3-dihydroxy6-nitro-7-sulfamoylbenzo[f-]quinoxaline) has been reported effective in preventing global and focal ischemic damage. Sheardown et al., *Science*, 247, 571 (1900); Buchan et al., *Neuroreport*, 2, 473 (1991); LePeillet et al., *Brain Research*, 571, 115 (1992). The noncompetitive AMPA receptor antagonist GKYI 52466 has been shown to be an effective neuroprotective agent in rat global ischemia models. LaPeillet et al., *Brain Research*, 571, 115 (1992). These studies strongly suggest that the delayed neuronal degeneration in brain ischemia involves glutamate excitotoxicity mediated at least in part by AMPA receptor activation. Thus, AMPA receptor antagonists may prove useful as neuroprotective agents and improve the neurological outcome of cerebral ischemia in humans.

SUMMARY OF THE INVENTION

The present invention provides an atropisomer of the formula I

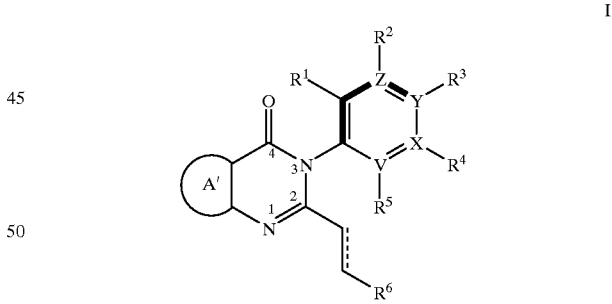

wherein either V, X, Y and Z are all carbon or one of them is nitrogen and the others are carbon;

each of $R^1$, $R^2$, $R^3$, $R^4$ and $R^5$ is selected, independently, from hydrogen, halogen, $(C_1-C_6)$alkyl, trifluoromethyl, cyano, $(C_1-C_6)$alkoxy, $(C_1-C_6)$alkylthio and $C(=O)-O-(C_1-C_6)$alkyl, with the proviso that: (a) $R_1$ can not be the same as $R^5$ when each of V, X and Z is carbon; (b) at least one of $R^1$ and $R^5$ must be other than hydrogen; and (c) when V, X, Y or Z is nitrogen, then $R^5$, $R^4$, $R^3$ or $R^2$, respectively, is absent;

ring A' is a fused heteroaromatic ring, wherein said heteroaromatic ring is a 5 or 6 membered heteroaromatic ring, wherein said 6 membered heteroaromatic ring, taken together with the carbon atoms common to both rings of the bicyclic system, has the formula

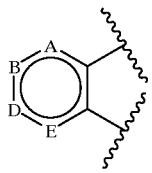

and wherein said 5 membered heteroaromatic ring, taken together with the carbon atoms common to both rings of the bicyclic system, has the formula

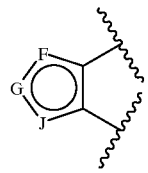

wherein said ring positions "A", "B", "D" and "E" may be independently selected from carbon or nitrogen;

wherein said ring positions "F", "G" and "J" may be independently selected from carbon, nitrogen, oxygen or sulfur, with the proviso that: (a) if more than two of "F", "G" or "J" is a heteroatom then said 5 membered heteroaromatic ring is selected from the group consisting of (1,2,3)-triazole, (1,2,3)-thiadiazole, (1,2,5)-thiadiazole, and (1,2,5)-oxadiazole; and (b) if two of "F", "G" or "J" are heteroatoms, only one of said heteroatoms may be oxygen or sulfur;

wherein said fused heteroaromatic rings may optionally be independently substituted on any of the carbon or nitrogen atoms capable of forming an additional bond with a substituent selected from hydrogen, $(C_1-C_6)$ alkyl, halogen, trifluoromethyl, amino-$(CH_2)_n$—, $(C_1-C_6)$alkylamino-$(CH_2)_n$—, di$(C_1-C_6)$alkyl-amino-$(CH_2)_n$—, $(C_1-C_6)$alkoxy, hydroxy$(C_1-C_6)$alkyl, $(C_1-C_6)$alkyl-O$(C_1-C_6)$alkyl-, —CN, $(C_1-C_6)$alkyl-CO—O—$(C_1-C_6)$alkyl-, $(C_1-C_6)$alkyl-O—CO—O—$(C_1-C_6)$alkyl, $(C_1-C_6)$alkyl-CO—O—, hydroxy, —NO$_2$, $R^{15}$—C(=O)—, $R^{15}$—O—C(=O)—, di$(C_1-C_6)$alkyl-N—C(=O)—, $(C_3-C_7)$cycloalkyl, and $R^{15}$—NH—C(=O)—, and phenyl optionally substituted with halo, $(C_1-C_6)$alkyl, —CN, or —CF$_3$;

$R^6$ is phenyl of the formula $P^1$ or a five or six membered heterocycle, wherein said 6-membered heterocycle has the formula

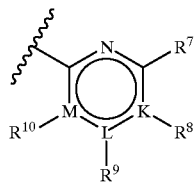

wherein "N" is nitrogen; wherein said ring positions "K", "L" and "M" may be independently selected from carbon or nitrogen, with the proviso that only one of "K", "L" or "M" can be nitrogen;

wherein said five membered heterocycle has the formula

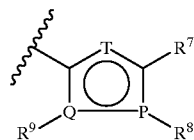

wherein said ring positions "P," "Q" and "T" may be independently selected from carbon, nitrogen, oxygen or sulfur; with the proviso that only one of "P," "Q" or "T" can be oxygen or sulfur and at least one of "P," "Q" or "T" must be a heteroatom;

wherein said "P$^1$ is a group of the formula

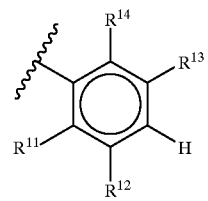

wherein each $R^{15}$ is, independently, hydrogen or $(C_1-C_6)$ alkyl;

each of $R^9$, $R^{10}$ and $R^{11}$ is selected, independently, from hydrogen, $(C_1-C_6)$alkyl optionally substituted with one to three halogen atoms, halo, CF$_3$, $(C_1-C_6)$alkoxy optionally substituted with one to three halogen atoms, $(C_1-C_6)$alkylthiol, $R^{16}$O—$(CH_2)_p$—, $(C_1-C_6)$alkyl-NH—$(CH_2)_p$—, di$(C_1-C_6)$alkyl-N—$(CH_2)_p$—, $(C_3-C_7)$cycloalkyl-NH—$(CH_2)_p$—, $H_2$N—(C=O)—$(CH_2)_p$—, $(C_1-C_6)$alkyl-HN—(C=O)—$(CH_2)_p$—, di$(C_{1-6})$alkyl-N—(C=O)—$(CH_2)_p$—, $(C_3-C_7)$cycloalkyl-NH—(C=O)—$(CH_2)_p$—, $R^{16}$O—(C=O)—$(CH_2)_p$—, $(C_1-C_6)$alkyl-(O=C)—O—$(C_1-C_6)$alkyl-, $(C_1-C_6)$alkyl-O—(O=C)—O—$(C_1-C_6)$-alkyl-, $(C_1-C_6)$alkyl-(O=C)—O—, $(C_1C_6)$alkyl-(O=C)—NH—$(CH_2)_p$—, H(O=C)—NH—$(CH_2)_p$—, $(C_1-C_6)$alkyl-(O=C)—N—[$(C_1-C_6)$alkyl]$(CH_2)_p$—, H(O=C)—N—[$(C_1-C_6)$alkyl]$(CH_2)_p$—, hydroxy, H—C(=O)—$(CH_2)_p$—, $(C_1-C_6)$alkyl—C(=O)—, $(C_1-C_6)$alkyl-O—C(=O)—, $R^{15}$—$(CH_2)_p$—O—C(=O)—, amino-$(CH_2)_p$—, hydroxy-$(C_1-C_6)$alkyl-, $C_1-C_6)$alkyl-O—$(C_1-C_6)$alkyl- and cyano;

each of $R^7$, $R^{12}$ and $R^{13}$ is selected, independently, from hydrogen, $(C_1-C_6)$alkyl optionally substituted with one to three halogen atoms, halogen, CF$_3$, $(C_1-C_6)$alkoxy optionally substituted with one to three halogen atoms, $(C_1-C_6)$alkylthiol, $R^{16}$O—$(CH_2)_p$—, $(C_1-C_6)$alkyl-NH—$(CH_2)_p$—, di$(C_1-C_6)$alkyl-N—$(CH_2)_p$—, $(C_3-C_7)$cycloalkyl-NH—$(CH_2)_p$—, $H_2$N—(C=O)—$(C_1-C_6)$alkyl-HN—(C=O)—$(CH_2)_p$—, di$(C_{1-6})$alkyl-N—(C=O)—$(CH_2)_p$—, $C_3-C_7)$cycloalkyl-NH—(C=O)—$(CH_2)_p$—, $R^{16}$O—(C=O)—$(CH_2)_p$—, $(C_{1-6})$alkyl-(O=C)—O—$(C_1-C_6)$alkyl-,$(C_1-C_6)$alkyl-O—(O=C)—O—$(C_1-C_6)$-alkyl-,$(C_1-C_6)$alkyl-(O=C)—O—, $(C_1-C_6)$alkyl-(O=C)—NH—$(CH_2)_p$—, H(O=C)—NH—$(CH_2)_p$—, $(C_{1-6})$alkyl-(O=C)-N-[$(C_{1-6})$alkyl]$(CH_2)_p$—, H(O=C)—N—[$(C_1-C_6)$alkyl]$(CH_2)_p$—, hydroxy, H—C(=O)—$(CH_2)_p$—, $(C_1-C_6)$alkyl-C(=O), $(C_1-C_6)$alkyl-O—C(=O)—, $R^{15}$—$(CH_2)_p$—O—C(=O)—, amino-$(CH_2)_p$—, hydroxy-$(C_1-C_6)$alkyl-, $(C_1-C_6)$alkyl-O—$(C_1-C_6)$ alkyl-, —CHO and cyano;

each $R^{14}$ is, hydrogen, halogen, cyano or trifluoromethyl,
$R^{16}$ is, hydrogen, $(C_1-C_6)$alkyl, $(C_1-C_6)$alkyl-(C=O)—, $(C_1-C_6)$alkyl-O—(C=O)—, $(C_1-C_6)$alkyl-NH—(C=O)—, or di$(C_1-C_6)$alkyl-N—(C=O)—;
$R^8$ is hydrogen, cyano, $(C_1-C_6)$alkyl, halogen, trifluoromethyl, —CHO or $(C_1-C_6)$alkoxy;

n is an integer from zero to 3;

p is an integer from zero to 3; and wherein the dashed line represents an optional double bond;

and the pharmaceutically acceptable salts of such compounds.

This invention also relates to atropisomers and their pharmaceutically acceptable salts that are defined as the atropisomers of formula I above, with the proviso that when $R^{11}$ is hydrogen, one of $R^{13}$ and $R^{14}$ is other than hydrogen.

The present invention also provides the pharmaceutically acceptable acid addition salts of atropisomers of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

This invention also provides a pharmaceutical composition for treating stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular damage, retinopathy, retinal neuropathy, tinnitus, idiopathic and drug induced Parkinson's Disease, anxiety, emesis, brain edema, chronic or acute pain, tardive dyskinesia or cerebral deficits subsequent to cardiac bypass surgery and grafting, in a mammal, comprising a pharmacologically-effective amount of an atropisomer of the formula I and a pharmaceutically acceptable carrier.

This invention also provides a method of treating stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular damage, retinopathy, retinal neuropathy, tinnitus, idiopathic and drug induced Parkinson's Disease, anxiety, emesis, brain edema, chronic or acute pain, tardive dyskinesia or cerebral deficits subsequent to cardiac bypass surgery and grafting, in a mammal, comprising administering to a mammal in need of such treatment a pharmacologically-effective amount of an atropisomer of the formula I, or a pharmaceutically acceptable salt thereof.

This invention also provides a pharmaceutical composition for treating a disorder or condition, the treatment or prevention of which can be effected or facilitated by reducing or inhibiting glutamate neurotransmission in a mammal, comprising a pharmacologically-effective amount of an atropisomer of the formula I, or a pharmaceutically effective salt thereof, and a pharmaceutically acceptable carrier.

This invention also provides a method of treating a disorder or condition, the treatment of which can be effected or facilitated by reducing or inhibiting glutamate neurotransmission in a mammal, comprising administering to a mammal in need of such treatment an amount of an atropisomer of the formula I, or a pharmaceutically effective salt thereof, that is effective in treating such disorder or condition.

This invention also provides a pharmaceutical composition for treating stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular damage, retinopathy, retinal neuropathy, tinnitus, idiopathic and drug induced Parkinson's Disease, anxiety, emesis, brain edema, chronic or acute pain, tardive dyskinesia or cerebral deficits subsequent to cardiac bypass surgery and grafting, in a mammal, comprising an AMPA receptor antagonizing effective amount of an atropisomer of the formula I, or a pharmaceutically salt thereof, and a pharmaceutically acceptable carrier.

This invention also provides a method for treating a condition selected from stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular damage, retinopathy, retinal neuropathy, tinnitus, idiopathic and drug induced Parkinson's Disease, anxiety, emesis, brain edema, chronic or acute pain, tardive dyskinesia and cerebral deficits subsequent to cardiac bypass surgery and grafting, in a mammal, comprising administering to a mammal requiring such treatment an AMPA receptor antagonizing effective amount of an atropisomer of the formula I, or a pharmaceutically acceptable salt thereof.

This invention also relates to a pharmaceutical composition for treating a disorder or condition, the treatment of which can be effected or facilitated by reducing or inhibiting glutamate neurotransmission in a mammal, comprising an AMPA receptor antagonizing effective amount of an atropisomer of the formula I, or a pharmaceutically acceptable salt thereof, and a pharmaceutically acceptable carrier.

This invention also relates to a method for treating a disorder or condition, the treatment of which can be effected or facilitated by reducing or inhibiting glutamate neurotransmission in a mammal, comprising administering to a mammal requiring such treatment an AMPA receptor antagonizing effective amount of an atropisomer of the formula I or a pharmaceutically acceptable salt thereof.

Unless otherwise indicated, the alkyl groups referred to herein, as well as the alkyl moieties of other groups referred to herein (alkoxy), may be linear or branched, and they may also be cyclic (eg, cyclopropyl, cyclobutyl, cyclopentyl, or cyclohexyl) or be linear or branched and contain cyclic moieties.

The term "treating" as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "pharmacologically-effective amount" as used herein means an amount sufficient to treat the stated disorder or condition or an AMPA receptor antagonizing effective amount, as the case may be.

Unless otherwise indicated, "halo" and "halogen", as used herein, refer to fluorine, bromine, chlorine or iodine.

Compounds of the formula I wherein the fused A' ring is a 6-membered aryl heterocycle include compounds wherein the ring positions A, B, D and E assume the following respective atom combinations:

| A | B | D | E |
|---|---|---|---|
| Nitrogen | Carbon | Carbon | Carbon |
| Carbon | Nitrogen | Carbon | Carbon |
| Carbon | Carbon | Nitrogen | Carbon |
| Nitrogen | Carbon | Nitrogen | Carbon |
| Carbon | Nitrogen | Carbon | Nitrogen |
| Nitrogen | Nitrogen | Carbon | Carbon |
| Carbon | Nitrogen | Nitrogen | Carbon |
| Carbon | Carbon | Nitrogen | Nitrogen |

| F | G | J |
|---|---|---|
| Nitrogen | Carbon | Carbon |
| Carbon | Nitrogen | Carbon |
| Carbon | Carbon | Nitrogen |
| Nitrogen | Nitrogen | Carbon |
| Nitrogen | Carbon | Nitrogen |
| Carbon | Nitrogen | Nitrogen |
| Nitrogen | Nitrogen | Nitrogen |
| Oxygen | Carbon | Carbon |
| Carbon | Oxygen | Carbon |
| Carbon | Carbon | Oxygen |
| Sulfur | Carbon | Carbon |
| Carbon | Sulfur | Carbon |
| Carbon | Carbon | Sulfur |
| Nitrogen | Oxygen | Carbon |
| Nitrogen | Carbon | Oxygen |
| Oxygen | Nitrogen | Carbon |
| Oxygen | Carbon | Nitrogen |
| Carbon | Oxygen | Nitrogen |
| Carbon | Nitrogen | Oxygen |
| Nitrogen | Sulfur | Carbon |
| Nitrogen | Carbon | Sulfur |
| Sulfur | Nitrogen | Carbon |
| Sulfur | Carbon | Nitrogen |
| Carbon | Sulfur | Nitrogen |
| Carbon | Nitrogen | Sulfur |
| Nitrogen | Nitrogen | Sulfur |
| Nitrogen | Sulfur | Nitrogen |
| Nitrogen | Oxygen | Nitrogen |

When $R^6$ is heteroaryl, one of ordinary skill in the art will understand that heteroaryl includes substituted or unsubstituted pyridin-2-yl, 1,3-pyrazin4-yl, 1,4-pyrazin-2-yl, 1,3-pyrimidin-2-yl, pyrrol-2-yl, 1,3-imidazol4-yl, 1,3-imidazol-2-yl, 1,3,4-triazol-2-yl, 1,3-oxazol-4-yl, 1,3-oxazol-2-yl, 1,3-thiazol-4-yl, 1,3-thiazol-2-yl, 1,2,4-oxadiazol-3-yl,1,2,4-oxadiazol-5-yl, fur-2-yl, 1,3-oxazol-5-yl, and 1,3,4-oxadiazol-2-yl, wherein said heteroaryl may optionally be substituted on any of the atoms capable of forming an additional bond, up to a maximum of three substituents.

Compounds of the formula I may have chiral centers and therefore may exist in different enantiomeric and diastereomic forms. This invention relates to all optical isomers and all stereoisomers of compounds of the formula I and mixtures thereof, and to all pharmaceutical compositions and methods of treatment defined above that contain or employ them, respectively.

Due to the substituent at position "2" and the carbonyl group at position "4" in the pyrimidin4-one of formula I, the ring attached to the nitrogen at position "3" cannot rotate freely. This restricted rotation means that compounds of the formula I exist in two isomeric forms or atropisomers. These atropisomers can be separated.

This invention relates to those stereoisomers of compounds of the formula I that are atropisomers. Atropisomers are isomeric compounds that are chiral, i.e., each isomer is not superimposable on its mirror image and the isomers, once separated, rotate polarized light in equal but opposite directions. Atropisomers are distinguished from enantiomers in that atropisomers do not possess a single asymmetric atom. Such compounds are conformational isomers which occur when rotation about a single bond in the molecule is prevented or greatly slowed as a result of steric interactions with other parts of the molecule and the substituents at both ends of the single bond are unsymmetrical. A detailed account of atropisomers can be found in Jerry March, *Advanced Organic Chemistry*, 101–102 (4th ed. 1992) and in Oki, *Top Stereochem.*, 14, 1–81(1983).

The bold lines in formula I above indicate that the bolded atoms, and the groups attached thereto, are sterically restricted so as to exist orthogonally above the plane of the fused pyrimidin4-one ring. This steric restriction is due to a rotational energy barrier preventing free rotation about the single bond connecting the nitrogen at position "3" of the bicyclic ring A' containing nucleus to the six membered V, X, Y and Z containing aromatic ring. This invention relates to all atropisomers represented by formula I above as well as the opposite atropisomers of all such compounds and all nonracemic mixtures of anyone or more atropisomers. The term "compounds of the formula I", as hereinafter referred to, is intended to include all atropisomers of this invention, i.e., those represented by formula I above, as well as the opposite atropisomers of such compounds and all nonracemic mixtures of one or more atropisomers selected from those depicted in formula I and their opposite atropisomers.

Formula I above includes compounds identical to those depicted but for the fact that one or more hydrogen or carbon atoms are replaced by isotopes thereof. Such compounds are useful as research and diagnostic tools in metabolism pharmokinetic studies and in binding assays. Specific applications in research include radioligand binding assays, autoradiography studies and in vivo binding studies.

Examples of preferred compounds of this invention are compounds of the formula I wherein $R^1$ is above the plane of the bicyclic A' ring containing nucleus of formula I.

Other examples of preferred compounds of this invention are compounds of the formula I wherein ring A' is thieno, $R^6$ is 2, 4 or 5-thiazolyl substituted with a methyl group, $R^1$ is chloro or methyl, Z is carbon or nitrogen and each of V, X and Y is carbon.

Other examples of preferred compounds of this invention are compounds of the formula I wherein ring A' is thieno, $R^6$ is 2, 4 or 5-thiazolyl substituted with a methyl group, $R^1$ is methyl or chloro, Z is nitrogen and each of V, X and Y is carbon.

Other examples of preferred compounds of this invention are compounds of the formula I wherein ring A' is thieno, $R^6$ is phenyl, 2chlorophenyl, 2-fluorophenyl, 2-bromophenyl or 2-hydroxyphenyl, each of $R^2$, $R^3$, $R^4$ and $R^5$, if present, is hydrogen, and $R^1$ is methyl or chloro.

Other examples of preferred compounds of this invention are compounds of the formula I wherein ring A' is thieno, $R^6$ is 2-pyridyl, each of V, X Y and Z is carbon each, of $R^2$, $R^3$, $R^4$ and $R^5$ is hydrogen, and $R^1$ is chloro or methyl.

Other examples of preferred compounds of this invention are compounds of the formula I wherein ring A' is thieno, $R^6$ is 2-fluorophenyl, Z is nitrogen, each of V, X and Y is carbon, each of $R^3$, $R^4$ and $R^5$ is hydrogen, and $R^1$ is chloro or methyl.

Throughout this application, the group of the formula

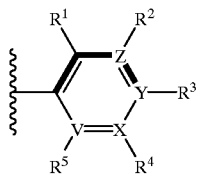

which appears in formula I, and the opposite atropisomers of such group, are referred to, collectively, as $R^{17}$.

DETAILED DESCRIPTION OF THE INVENTION

The compounds of formula I can be prepared according to the methods of Schemes 1 and 2. In the reaction Schemes and discussion that follow, A', A, B, D, E, F, G, J, K, L, M, P, Q, T, V, X, Y, Z, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $Ph^1$, n and p, unless otherwise indicated, are defined as above for formula I.

SCHEME 1

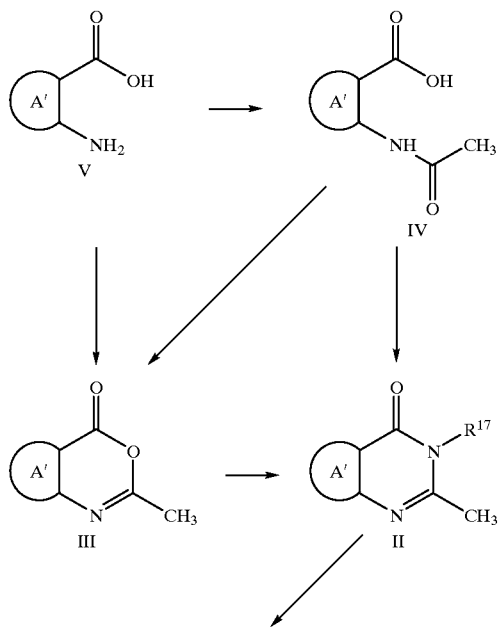

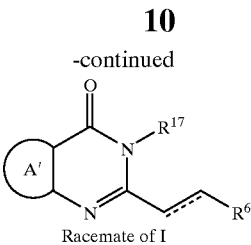

Racemate of I

SCHEME 2

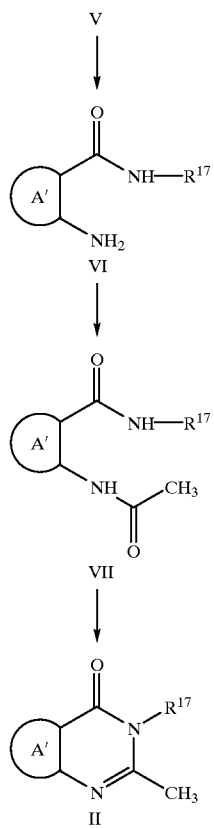

Scheme 1 refers to the preparation of compounds of the formula I from compounds of the formula V. Compounds of the formula V are commercially available or can be prepared by methods well known to those of ordinary skill in the art. Compounds of the formula V, wherein A' is a 4-amino-(1, 2)-pyridazine-5-carboxylic acid can be prepared according to the methods described in *J. Het. Chem.*, 14, 1099 (1977); *Aust. J. Chem.*, 22, 1745 (1969); and *J. Het. Chem.*, 5, 845 (1968). Compounds of the formula V wherein "A" is a 4-amino-(1,2)-pyridazine-3-carboxylic acid can be made according to the methods described in *J. Het. Chem.*, 5, 523 (1968). Compounds of the formula V, wherein A' is 2-amino-(1,2)-pyridazine-3carboxylic acid can be made according to the methods described in *J. Het. Chem.*, 5, 523 (1968); and *J. Org. Chem.*, 50, 346 (1995). Compounds of the formula V, wherein A' is 5-amino-(1,2,3)-thiazdiazole4-carboxylic acid can be prepared according to the methods described in *Chem. Berichte*, 99, 1618 (1966). Compounds of the formula V, wherein A' is 4-amino-(1,2,5)-thiadiazole-3-carboxylic acid can be made according to the methods described in *J. Med. Chem.*, 22, 944 (1979) and *Tetrahedron Lett.*, 2143 (1971). Compounds of the formula V, wherein A' is 4-amino-(1,2,5)-oxadiazole-3-carboxylic acid can be made according to the methods described in *Heterocycles*, 20, 2351 (1983). Compounds of the formula V, wherein A' is 3-amino-thiophene-2-carboxylic acid can be prepared according to the method described in European Patent publication 269,295 published June 1, 1988.

A compound of the formula V can be converted into an acetamide of the formula IV by reacting it with acetyl chloride or acetic anhydride, in the presence of a base, in a reaction inert solvent. Suitable solvents include methylene chloride, dichloroethane, tetrahydrofuran and dioxane. Methylene chloride is the preferred solvent. Suitable bases include trialkylamines (e.g., triethylamine and tributylamine), dimethylaminopyridine and potassium carbonate. Triethylamine is preferred. The temperature of this reaction can range from about 0° C. to about 35° C., and is preferably about 30° C. The reaction is generally carried out for about 1 hour to about 10 hours, preferably for about 3 hours.

The acetamide of the formula IV can be cyclized to form a compound of the formula III by reacting it with a dehydrating agent, in the presence of a catalyst, in a dry reaction inert solvent. Suitable dehydrating agents include acetic anhydride, phosphrous pentoxide, dicyclohexylcarbodiimide and acetyl chloride. Acetic anhydride is preferred. Examples of catalysts that can be used are sodium or potassium acetate, acetic acid, p-toluene sulfonic acid, and boron trifluoride etherate. The preferred catalyst is sodium acetate. This reaction is generally carried out in a dry reaction inert solvent such as dioxane, toluene, diglyme or dichloroethane. It is preferably carried out in dioxane. The temperature of this reaction can range from about 80° C. to about 110° C. The reaction is typically carried out for about 1 hour to about 24 hours. Preferably, the reaction is conducted at about 100° C. for about 3 to 10 hours.

Alternatively, the compound of formula V can be directly converted into a compound of formula III by reacting it with acetic anhydride, in the presence of an acid catalyst, in a solvent. Suitable acid catalysts include acetic acid, sulfuric acid, and p-toluene sulfonic acid. Suitable solvents include acetic acid, toluene and xylene. Acetic acid is the preferred catalyst and the preferred solvent. The temperature of this reaction can range from about 20° C. to about 150° C. for about 10 minutes to about 10 hours. Preferably, the reaction is carried out at about 120° C. for about 2 to 5 hours.

The compound of formula III, formed by either of the above methods, can then be reacted with an amine of the formula $R^{17}NH_2$ in a polar protic solvent, in the presence of an acid catalyst, to form a compound of the formula II. Suitable acid catalysts include acetic acid, p-toluene sulfonic acid and sulfuric acid. Suitable polar protic solvents include acetic acid, methanol, ethanol and isopropanol. Acetic acid is the preferred catalyst and the preferred solvent. The temperature of this reaction can range from about 20° C. to about 117° C. and is preferrably about 117° C. The reaction is generally allowed to run for about 1 hour to about 24 hours. It is preferably allowed to run for about 6 hours.

Alternatively, a compound of the formula IV can be converted directly into a compound of the formula II by reaction with a dehydrating agent, an amine of the formula $R^{17}NH_2$, and a base, in a reaction inert solvent. Examples of appropriate dehydrating agents are phosphorous trichloride, phosphorous oxychloride, phosphorous pentachloride and thionyl chloride with phosphorous trichloride being preferred. Suitable bases include pyridine, lutidine, dimethylaminopyridine, triethylamine and N-methyl morpholine, with pyridine being preferred. Suitable solvents include toluene, cyclohexane, benzene and xylene. Toluene is the preferred solvent. Under some circumstances, when the combined reactants are a liquid, the reaction may be run neat. The temperature of the reaction can range from about 50° C. to about 150° C. for about 1 hour to about 24 hours. The reaction is preferably conducted at about 110° C. for about 4 hours.

Reaction of the compound of formula II with an aldehyde of the formula $R^6CHO$ in the presence of a catalyst and a dehydrating agent, in a suitable solvent, yeilds the corresponding compound of formula I. The catalyst is selected from zinc chloride, aluminum chloride, tin chloride, and boron trifluoride etherate, and is preferably zinc chloride. The dehydrating agent is selected from acetic anhydride and propionic anhydride, and is preferably acetic anhydride. Suitable polar solvents include acetic acid and propionic acid. The temperature of this reaction can range from about 60° C. to about 100° C. for about 30 minutes to about 24 hours. Preferably, the reaction is carried out at about 100° C. for about 3 hours.

Alternatively, a compound of the formula V can be converted into a compound of the formula II according to the methods illustrated in Scheme 2. The compound of formula II, so formed, can then be converted into a compound of formula I according to the methods of Scheme 1. Referring to Scheme 2, a compound of the formula V is reacted with a coupling reagent, an amine of the formula $R^{17}NH_2$, and a base, in a reaction inert solvent, to form a compound of the formula VI. Appropriate coupling reagents are those that activate the carboxylic functionality, such as dicyclohexylcarbodiimide, N-3-dimethylaminopropyl-N'-ethylcarbodiimide, 2-ethoxy-1-ethoxycarbonyl-1,2-dihydroquinoline (EEDQ), carbonyl diimidazole (CDI), and diethylphosphorylcyanide. Suitable bases include dimethylaminopyridine (DMAP), hydroxybenzotriazole (HBT) and triethylamine. Dimethylaminopyridine is preferred. The coupling is conducted in an inert solvent, preferably an aprotic solvent such as acetonitrile, dichloromethane, dichloroethane, or dimethylformamide. The preferred solvent is dichloromethane. The temperature of this reaction can generally range from about −30 to about 80° C., and is preferably from about 0 to about 25° C.

The compound of formula VI so formed can be converted into a compound of the formula VII by reaction with acetyl chloride or acetic anhydride in the presence of a base such as a trialkylamine (eg., triethylamine or tributylamine), dimethylaminopyridine or potassium carbonate, preferably triethylamine, in a solvent such as methylene chloride, tetrahydrofuran or chloroform, preferably methylene chloride, at a temperature from about 0° C. to about 35° C., for about 1 hour to about 10 hours, preferably at about 30° C. for about 3 hours.

Cyclization of the compound of formula VII by reaction with triphenylphosphine, a base, and a dialkyl azodicarboxylate in a reaction inert solvent yeilds the coresponding compound of formula II. Bases suitable for use in this reaction include pyridine, triethylamine and 4-dimethylaminopyridine. 4-Dimethylaminopyridine is preferred. Examples of solvents that can be used include dimethylformamide, tetrahydrofuran and dioxane, with dioxane being preferred. The temperature of the reaction can range from about 25° C. to about 125° C. for about 1 hour to about 24 hours. The reaction is preferably carried out at about 100° C. for about 8 to 15 hours. The resulting compound of formula II can then be converted into the corresponding compound of formula I according to the method described in Scheme 1.

Compounds of formula II can also be made according to the methods described in Miyashita, et al., *Heterocycles*, 42, 2,691–699 (1996).

The compounds prepared by the methods of Schemes 1 and 2 are racemic mixtures of atropisomers. In order to obtain the pure individual atropisomers, the racemic mixtures must be separated. This separation may be achieved by high performance liquid chromatography using a chiral column. Examples of suitable chiral columns include Chiral pak AD and Chiral cel OA, OB, OC, OD and OK, but other chiral columns can also be used. With the appropriate chiral column, the individual atropisomers will elute with different retention times. Collection and concentration of the eluent from the individual atropisomers will afford the pure atropisomers.

Alternatively, for racemic mixtures of atropisomers that contain an acidic or basic moiety, chiral resolution may be achieved by forming diastereomeric salts with optically pure acids (for example, tartaric acid) when the racemate contains a basic moiety or with optically pure bases (for example a-methylbenzyl amine) when the racemate contains an acidic moiety. Repeated recrystallizations of these diastereomeric salts will allow the single pure atropisomer to be obtained. The single pure atropisomer can be used directly as a salt or may be neutralized to obtain the free base or free acid atropisomer.

For those atropisomers that can be racemized upon heating, it may be possible to effect a chiral resolution by carrying out the diastereomeric salt recrystallization referred to above at a temperature at which the atropismomers readily interconvert. Under such conditions, all of the racemic material can be funneled into the desired atropisomer as it crystallizes out of solution. This is the preferred method of carrying out the above chiral salt resolution in that it provides yields approaching 100%.

Unless indicated otherwise, the pressure of each of the above reactions is not critical. Generally, the reactions will be conducted at a pressure of about one to about three atmospheres, preferably at ambient pressure (about one atmosphere).

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

The compounds of the formula I and the pharmaceutically acceptable salts thereof (hereinafter, also referred to as the active compounds of the invention) are useful for the treatment of neurodegenerative, psychotropic and drug or alcohol induced deficits and are potent AMPA receptor antagonists. The active compounds of the invention may therefore be used in the treatment or prevention of stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular damage, retinopathy, retinal neuropathy, tinnitus, idiopathic and drug induced Parkinson's Disease, anxiety, emesis, brain edema, chronic or acute pain, tardive dyskinesia and cerebral deficits subsequent to cardiac bypass surgery and grafting.

The in vitro and in vivo activity of the compounds of the invention for AMPA receptor antagonism can be determined by methods available to one of ordinary skill in the art. One method for determining the activity of the compounds of the invention is by inhibition of pentylenetetrazol (PTZ)-induced seizures. Another method for determining the activity of the compounds of the invention is by blockade of AMPA receptor activation-induced $^{45}Ca^{2+}$ uptake.

One specific method for determining inhibition of pentylenetetrazol (PTZ)-induced seizures is as follows. The activity of the compounds of the invention for inhibition of pentylenetetrazol (PTZ)-induced seizures in mice can be determined according to the following procedure. This assay examines the ability of compounds to block seizures and death produced by PTZ. Measures taken are latency to clonic and tonic seizures, and death. $ID_{50}$s are determined based on percent protection.

Male CD-1 mice from Charles River, weighing 14–16 g on arrival and 25–35 g at the time of testing, serve as subjects for these experiments. Mice are housed 13 per cage under standard laboratory conditions on a L:D/7 a.m.: 7 p.m. lighting cycle for at least 7 days prior to experimentation. Food and water are available ad libitum until the time of testing.

All compounds are administered in a volume of 10 ml/kg. Drug vehicles will depend on compound solubility, but screening will typically be done using saline, distilled water, or E:D:S/5:5:90 (5% emulphor, 5% DMSO, and 90% saline) as the injection vehicle.

Mice are administered the test compounds or vehicle (i.p., s.c., or p.o.) and are placed into plexiglass cages in groups of five. At a predetermined time after these injections, mice are given an injection of PTZ (i.p., 120 mg/kg) and placed into individual plexiglass cages. Measures taken during this five minute test period are: (1) latency to clonic seizures, (2) latency to tonic seizures, and (3) latency to death. Treatment groups are compared to the vehicle-treated group by Kruskal-Wallis Anova and Mann-Whitney U tests (Statview). Percent protection is calculated for each group (number of subjects not showing seizure or death as indicated by a score of 300 secs) at each measure. $ID_{50}$'s are determined by prohibit analysis (Biostat).

Another method for determining the activity of the compounds is to determine the effect of the compounds on motor coordination in mice. This activity can be determined according to the following procedure.

Male CD-1 mice from Charles River, weighing 14–16 g on arrival and 23–35 g at the time of testing, serve as subjects for these experiments. Mice are housed 13 per cage under standard laboratory conditions on a L:D/7 a.m.: 7 p.m. lighting cycle for at least 7 days prior to experimentation. Food and water are available ad libitum until the time of testing.

All compounds are administered in a volume of 10 ml/kg. Drug vehicles will depend on compound solubility, but screening will typically be done using saline, distilled water, or E:D:S/5:5:90 (5% emulphor, 5% DMSO, and 90% saline) as the injection vehicle.

The apparatus used in these studies consists of a group of five 13.34×13.34 cm wire mesh squares suspended on 11.43 cm steel poles connected to a 165.1 cm pole which is elevated 38.1 cm above the lab bench. These wire mesh squares can be turned upside-down.

Mice are administered test compounds or vehicle (i.p., s.c., or p.o) and are placed into plexiglass cages in groups of five. At a predetermined time after these injections, mice are placed on top of the wire mesh squares and flipped so that they are suspended upside-down.

During the one minute test, mice are rated 0 if they fall off the screen, 1 if they hang on upside-down, or 2 if they climb up onto the top. Treatment groups are compared to the vehicle-treated group with Kruskal-Wallis and Mann-Whitney U tests (Statview).

One specific method for determining blockade of AMPA receptor activation-induced $^{45}Ca^{2+}$ uptake is described below.

Neuronal Primary Cultures

Primary cultures of rat cerebellar granule neurons are prepared as described by Parks, T. N., Artman, L. D., Alasti, N., and Nemeth, E. F., *Modulation Of N-Methyl-D-Aspartate Receptor-Mediated Increases In Cytosolic Calcium In Cultured Rat Cerebellar Granule Cells*, Brain Res. 552, 13–22 (1991). According to this method, cerebella are removed from 8 day old CD rats, minced into 1 mm pieces and incubated for 15 minutes at 37° C. in calcium-magnesium free Tyrode's solution containing 0.1% trypsin. The tissue is then triturated using a fine bore Pasteur pipette. The cell suspension is plated onto poly-D-lysine coated 96-well tissue culture plates at $10^5$ cells per well. Medium consists of Minimal Essential Medium (MEM), with Earle's salts, 10% heat inactivated Fetal Bovine Serum, 2 mM L-glutamine, 21 mM glucose, Penicillin-Streptomycin (100 units per ml) and 25 mM KCI. After 24 hours, the medium is replaced with fresh medium containing 10 mM cytosine arabinoside to inhibit cell division. Cultures should be used at 6–8 DIV.

AMPA Receptor Activation-induced $^{45}Ca^{2+}$ uptake

The effects of drugs on AMPA receptor activation-induced $^{45}Ca^{2+}$ uptake can be examined in rat cerebellar granule cell cultures. Cultures in 96 well plates are preincubated for approximately 3 hours in serum free medium and then for 10 minutes in a $Mg^{2+}$-free balanced salt solution (in mM: 120 NaCl, 5 KCl, 0.33 $NaH_2PO_4$ 1.8 $CaCl_2$, 22.0 glucose and 10.0 HEPES at pH 7.4) containing 0.5 mM DTT, 10 uM glycine and drugs at 2× final concentration. The reaction is started by rapid addition of an equal volume of the balanced salt solution containing 100 mM of the AMPA receptor agonist kainic acid and $^{45}Ca^{2+}$ (final specific activity 250 Ci/mmol). After 10 minutes at 25° C., the reaction is stopped by aspirating the $^{45}Ca^{2+}$-containing solution and washing the cells 5× in an ice cold balanced salt solution containing no added calcium and 0.5 mM EDTA. Cells are then lysed by overnight incubation in 0.1% Triton-X100 and radioactivity in the lysate is then determined. All of the compounds of the invention, that were tested, had $IC_{50}S$ of less than 5 mM.

The compositions of the present invention may be formulated in a conventional manner using one or more pharmaceutically acceptable carriers. Thus, the active compounds of the invention may be formulated for oral, buccal, transdermal (eg., patch), intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., stroke) is 0.01 to 50 mg/kg of the active ingredient per unit dose which could be administered, for example, 1 to 4 times per day.

Aerosol formulations for treatment of the conditions referred to above (e.g., stroke) in the average adult human are preferably arranged so that each metered dose or "puff" of aerosol contains 20 mg to 1000 mg of the compound of the invention. The overall daily dose with an aerosol will be within the range 100 mg to 10 mg. Administration may be several times daily, for example 2, 3, 4 or 8 times, giving for example, 1, 2 or 3 doses each time.

The following Examples illustrate the preparation of the compounds of the present invention. Commercial reagents were utilized without further purification. Melting points are uncorrected. All NMR data were recorded at 250, 300 or 400 MHz in deuterochloroform unless otherwise specified and are reported in parts per million (d) and are referenced to the deuterium lock signal from the sample solvent. All non-aqueous reactions were carried out in dry glassware with dry solvents under an inert atmosphere for convenience and to maximize yields. All reactions were stirred with a magnetic stirring bar unless otherwise stated. Unless otherwise stated, all mass spectra were obtained using chemical impact conditions. Ambient or room temperature refers to 20–25° C. Melting points are uncorrected.

EXAMPLE 1

3-(2-Methyl-phenyl)-2-[2-(2-fluoro-phenyl)-vinyl]-3H-thieno[3,2-d]pyrimidin-4-one Anhydrous zinc chloride (7.0 g, 51.4 mmol) was fused with a nitrogen purge in a round bottom flask with an open flame. The reaction vessel was allowed to return to ambient temperature, then dioxane (100 mL) was added. To this mixture was added 2-methyl-3-(2-methylphenyl)-3H-thieno[3,2-d]pyrimidin-4-one (7.0 g, 27.34 mmol, preparation 2), acetic anhydride (7.7 mL, 82.0 mmol), and 2-fluorobenzaldehyde (8.6 mL, 10.2 mmol). The reaction was refluxed 14 hours, cooled to ambient temperature, and partitioned between ethyl acetate and water. The aqueous layer was extracted with ethyl acetate and the combined organic layer was filtered to obtain a small amount of product which had precipitated. The filtrate was washed with water and brine, dried over magnesium sulfate and concentrated to leave a mustard colored solid. This material was added to the product which had previously been collected and the combined material was flash chromatographed on silica gel (60×185 mm) eluting with 25–40% ethyl acetate/hexane to afford 5.06 g (51%) of 3-(2-methyl-phenyl)-2-[2-(2-fluoro-phenyl)-vinyl]-3H-thieno[3,2-d]pyrimidin-4-one as a light yellow solid.

Mp 220–221° C.; $^1$H NMR δ8.03 (d, J=15.8 Hz, 1 H), 7.82 (d, J=5.2 Hz, 1 H), 7.45–7.37 (m, 4 H), 7.25–7.10 (m, 3 H), 7.07–6.99 (m, 2 H), 6.44 (d, J=15.9 Hz, 1 H), 2.11 (s, 3 H). Analysis calculated for $C_{21}H_{15}FN_2OS$: C, 68.76; H, 4.23; N, 7.64. Found: C, 68.89; H, 4.16; N, 7.72.

EXAMPLE 2

3-(2-Chloro-phenyl)-2-[2-(2-fluoro-phenyl)-vinyl]-3H-thieno[3,2-d]pyrimidin-4-one To a mixture of fused zinc chloride (0.35 g, 2.56 mmol) and dioxane (15 mL), 2-methyl-3-(2-chlorophenyl)-3H-thieno[3,2-d]pyrimidin-4-one (0.344 g, 1.24 mmol, preparation 3), and acetic anhydride (0.35 mL, 3.73 mmol) was added 2-fluorobenzaldehyde (0.39 mL, 3.73 mmol). The reaction was refluxed 30 hours, cooled to ambient temperature, and diluted with ethyl acetate and water. The two phase mixture was treated with aqueous sodium bicarbonate until the aqueous layer remained basic. Phases were filtered to remove an insoluble residue, then separated. The aqueous layer was extracted with ethyl acetate and the combined organic layer was washed with water and brine, dried over sodium sulfate and concentrated to leave a brown residue. This material was taken up in ethyl acetate and diluted with hexane until a precipitate (0.153 g, 32%) of 3-(2-chloro-phenyl)-2-[2-(2-fluoro-phenyl)-vinyl]-3H-thieno[3,2-d]pyrimidin-4-one formed, as a yellow solid.

Mp 215–216° C.; $^1$H NMR δ8.05 (d, J=15.5 Hz, 1 H), 7.84 (d, J=5.2 Hz, 1 H), 7.65–7.61 (m, 1 H), 7.51–7.40 (m, 2 H), 7.39–7.36 (m, 1 H), 7.29–7.22 (m, 2 H), 7.08–7.00 (m, 2 H), 6.42 (d, J=15.5 Hz, 1 H). Analysis calculated for $C_{20}H_{12}FClN_2OS$: C, 62.75; H, 3.14; N, 7.32. Found: C, 62.45; H, 3.14; N, 7.40.

EXAMPLE 3

3-(2-Methyl-phenyl)-2-[2-pyrid-2-yl-vinyl]-3H-thieno[3,2-d]pyrimidin-4-one

To a mixture of fused zinc chloride (2.13 g, 15.6 mmol) and dioxane (75 mL), 2-methyl-3-(2-methylphenyl)-3H-thieno[3,2-d]pyrimidin-4-one (2.0 g, 7.81 mmol, preparation 2), and acetic anhydride (2.2 mL, 23.4 mmol) was added 2-pyridine carboxaldehyde (2.2 mL, 23.4 mmol). The reaction was refluxed 1.5 hours, cooled to ambient temperature, and diluted with aqueous sodium bicarbonate. The mixture was extracted with ethyl acetate and the organic extracts were washed with water and brine, dried over sodium sulfate and concentrated to leave a dark residue. This material was flash chromatographed on silica gel (45×125 mm). Elution with 20% ethyl acetate/hexane removed an unweighed impurity. Continued elution with 40% ethyl acetate/hexane gave a sticky yellow foam. The foam was triturated with 5% ethyl acetate/hexane to yield 1.9 g (70%) of 3-(2-methyl-phenyl)-2-[2-pyrid-2-yl-vinyl]-3H-thieno[3,2-d]pyrimidin-4-one as a yellow solid.

Mp 203° C.; $^1$H NMR δ8.47 (d, J=3 Hz, 1 H), 7.92 (d, J=14.7 Hz, 1 H), 7.82 (d, J=4 Hz, 1 H), 7.60 (t, J=8.5 Hz, 1 H), 7.43–7.37 (m, 4 H), 7.26–7.12 (m, 3 H), 6.89 (d, J=14.7 Hz, 1 H), 2.10 (s, 3 H). Analysis calculated for $C_{20}H_{15}N_3OS$: C, 69.36; H, 4.62; N, 12.14. Found: C, 69.10; H, 4.50; N, 12.19.

EXAMPLE 4

The compounds in Table 1 were all made by essentially the same procedure as exemplified in Examples 1–3.

TABLE 1

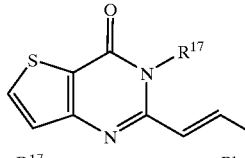

| R⁶ | R¹⁷ | Physical Data |
|---|---|---|
| 2-chlorophenyl | 2-methylphenyl | mp 198° C.<br>¹H NMR δ 8.29 (d, J = 15.4 Hz, 1 H), 7.82 (d, J = 5.2 Hz, 1 H), 7.43–7.36 (m, 5 H), 7.23–7.12 (m, 4 H), 6.31 (d, J = 15.5 Hz, 1 H), 2.11 (s, 3 H) HRMS M⁺¹ calculated m/e = 379.0669. Observed m/e = 379.0684. |
| 2-bromophenyl | 2-methylphenyl | mp 194° C.<br>¹H NMR δ 8.24 (d, J = 15.5 Hz, 1 H), 7.82 (d, J = 5.3 Hz, 1 H), 7.55 (d, J = 6.6 Hz, 1 H), 7.44–7.37 (m, 4 H), 7.24–7.12 (m, 4 H), 6.27 (d, J = 15.6 Hz, 1 H), 2.11 (s, 3 H)<br>Analysis calculated for C₂₁H₁₅BrN₂OS.H₂O: C, 57.14; H, 3.85; N, 6.35. Found: C, 57.36; H, 3.59; N, 6.23. |
| 2-fluorophenyl | 2-trifluoromethylphenyl | mp 206–207° C.<br>¹H NMR δ 8.01 (d, J = 15.4 Hz, 1 H), 7.93–7.69 (m, 4 H), 7.42–7.38 (m, 2 H), 7.38–7.21 (m, 2 H), 7.07–7.02 (m, 2 H), 6.35 (d, J = 15.5 Hz, 1 H) |
| pyrid-2-yl | 2-chlorophenyl | mp 204–205° C.<br>¹H NMR δ 8.49–8.47 (m, 1 H), 7.94 (d, J 15.3 Hz, 1 H), 7.84 (d, J = 4.6 Hz, 1 H), 7.65–7.59 (m, 2 H), 7.53–7.47 (m, 2 H), 7.42–7.37 (m, 2 H), 7.29 (d, J = 7 Hz, 1 H), 7.16–7.13 (m, 1 H), 6.93 (d, J = 15.3 Hz, 1 H) Analysis calculated for C₁₉H₁₂ClN₃OS: C, 62.39; H. 3.28; N, 11.49. Found: C, 62.71; H, 3.35; N, 11.45. |
| 2-methoxyphenyl | 2-chlorophenyl | mp 90–91° C.<br>¹H NMR δ 8.15 (d, J = 15 6 Hz, 1 H), 7.83 (d, J 5.3 Hz, 1 H), 7.66–7.63 (m, 1 H), 7.50 (sym m, 2 H), 7.41–7.33 (m, 2 H), 7.29–7.23 (m, 2 H), 6.90–6.82 (m, 2 H), 6.55 (d J = 15.5 Hz, 1 H), 3.71 (s, 3 H) |
| 4-methoxyphenyl | 2-chlorophenyl | mp 88–89° C.<br>¹H NMR δ 7.93 (d, J = 15.4 Hz, 1 H), 7.83 (d J = 5.2 Hz, 1 H), 7.66–7.63 (m, 1 H), 7.51 (sym m, 2 H), 7.41–7.36 (m, 2 H), 7.27–7.24 (m, 2 H), 6.82 (d, J = 8.8 Hz, 1 H), 6.13 (d, J = 15.4 Hz, 1 H), 3.79 (s, 3 H) |
| 4-carbomethoxy-phenyl | 2-methylphenyl | mp 187–188° C.<br>¹H NMR δ 7.98–7.92 (m, 3 H), 7.85 (d, J = 5.2 Hz, 1 H), 7.50–7.38 (m, 4 H), 7.32 (d, J = 8.3 Hz, 2 H), 7.21 (d, J = 7.8 Hz, 1 H), 6.39 (d, J = 15.6 Hz, 1 H), 3.89 (s, 3 H), 2.12 (s,3 H) |
| 2-hydroxyphenyl | 2-chlorophenyl | mp 245° C.<br>¹H NMR δ 8.29 (d, J = 15.5 Hz, 1 H), 7.86 (d, J = 5.3 Hz, 1 H), 7.63–7.59 (m, 1 H), 7.50–7.44 (m, 4 H), 7.39–7.36 (m, 2 H), 7.11 (t, J = 8 Hz, 1 H), |

TABLE 1-continued

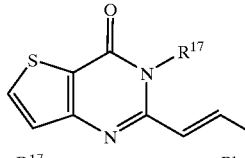

| R6 | R17 | Physical Data |
|---|---|---|
| | | 6.81–6.76 (m, 1 H), 6.69 (d, J = 8 Hz, 1 H), 5.95 (d, J = 15.7 Hz, 1 H) |
| pyrid-2-y | 2-bromophenyl | mp 221° C.<br>$^1$H NMR δ 8.48 (d, J = 4.7 Hz, 1 H), 7.95 (d, J = 15 Hz, 1 H), 7.85 (d, H = 5.4 Hz, 1 H), 7.80 (dd, J = 1.4, 8 Hz, 1 H), 7.63 (dt, J = 1.8, 7.7 Hz, 1 H), 7.54 (dt, J = 1.5, 7.5 Hz, 1 H), 7.46–7.33 (m, 3 H), 7.29 (d, J = 7.9 Hz, 1 H), 7.18–7.14 (m, 1 H), 6.92 (d, J = 15 Hz, 1 H) |
| 2-fluorophenyl | 2-chloropyrid-3-yl | Isolated as hydrochloride salt. mp 234–236° C.<br>$^1$H NMR (DMSO d$_6$) δ 8.68 (dd, J = 1.8, 4.8 Hz, 1 H), 8.36 (d, J = 5.3 Hz, 1 H), 8.29 (dd, J = 1.9, 7.8 Hz, 1 H), 7.98 (d, J = 15.6 Hz, 1 H), 7.76 (dd, J = 4.8, 7.8 Hz, 1 H), 7.59 (d, J = 5.2 Hz, 1 H), 7.48–7.38 (m, 1 H), 7.28–7.18 (m, 2 H), 6.49 (d, J = 15.6 Hz, 1 H) |
| 2-methoxyphenyl | 2-methylphenyl | mp 154° C.<br>$^1$H NMR δ 8.13 (d, J = 15.6 Hz, 1 H), 7.81 (d, J = 5.2 Hz, 1 H), 7.42 (sym m, 4 H), 7.25–7.20 (m, 3 H), 6.89–6.81 (m, 2 H), 6.58 (d, J = 15.5 Hz, 1 H), 3.69 (s, 3 H), 2.11 (s, 3 H) |
| 2-hydroxyphenyl | 2-methylphenyl | mp >256° C.<br>$^1$H NMR (DMSO d$_6$) δ 8.28 (d, J = 5.4 Hz, 1 H), 8.07 (d, J = 15.7 Hz, 1 H), 7.53 (d, J = 5.3 Hz, 1 H), 7.50–7.36 (m, 4 H), 7.18–7.12 (m, 2 H), 6.84 (d, J = 8 Hz, 1 H), 6.75 (t, J = 7.5 Hz, 1 H), 6.52 (d, J = 5.5 Hz, 1 h), 2.02 (s, 3 H) |
| pyrid-2-yl | 2-chloropyrid-3-yl | mp 244° C.<br>$^1$H NMR δ 8.61 (dd, J = 1.8, 4.8 Hz, 1 H), 8.48 (d, J = 4.3 Hz, 1 H), 7.96 (d, J = 14.8 Hz, 1 H), 7.88 (d, J = 5.2 Hz, 1 H), 7.80 (dd, J = 1.8, 7.8 Hz, 1 H), 7.65 (dt, J = 1.8, 7.7 Hz, 1 H), 7.52 (dd, J = 4.8, 7.8 Hz, 1 H), 7.43 (d, J = 5.2 Hz, 1 H), 7.31 (d, J = 7.8 Hz, 1 H), 7.21–7.16 (m, 1 H), 6.93 (d, J = 14.8 Hz, 1 H) |
| 4-methyl-(1,3)-thiazol-2-yl | 2-methylphenyl | mp 198–200° C.<br>$^1$H NMR δ 7.99 (d, J = 15.2 Hz, 1H), 7.82 (dd, J = 1.1,5.3 Hz, 1H), 7.41 (m, 4H), 7.18 (d, J = 7.5 Hz, 1H), 6.85 (s, 1H), 6.59 (d, J = 15.1 Hz, 1H), 2.39 (s, 3H), 2.10 (s, 3H). |
| 2-methylthiazol-4-yl | 2-chloropyrid-3-yl | mp 206–208° C.<br>NMR δ 8.60 (m, 1 H), 7.90 (d, J = 14.8 Hz, 1 H), 7.86 (dd, J = 0.7,5.2 Hz, 1 H), 7.78 (m, 1 H), 7.51 (dd, J = 4.8, 7.7 Hz, 1 H), 7.41 (d, J = 5.4 Hz, 1 H), 7.25 (s, 1 H), 6.61 (d, J = 14.7 Hz, 1 H), 2.63 (s, 3 H). |

TABLE 1-continued

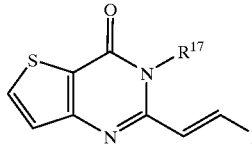

| R[6] | R[17] | Physical Data |
|---|---|---|
| 2-methylthiazol-4-yl | 2-methylpyrid-3-yl | mp 215° C.<br>NMR δ 8.67 (br d, J = 4.2 Hz, 1 H), 7.88–7.83 (m, 2 H), 7.56 (d, J = 7.5 Hz, 1 H), 7.38 (m, 2 H), 7.20 (s, 1 H), 6.57 (d, J = 14.8 Hz, 1 H), 2.59 (s, 3 H), 2.37 (s, 3 H). |
| 2-methyl-1,3-thiazol-4-yl | 2-methylphenyl | mp 246–247° C.<br>$^1$H NMR δ 7.89 (d, J = 15 Hz, 1H), 7.77 (m, 1H), 7.43 (m, 4H), 7.25 (s, 1H), 7.19 (s, 1H), 6.62 (d, J = 14.9 Hz, 1H), 2.61 (s, 3H), 2.11 (s 3H). |

EXAMPLE 5

The compounds in Table 2 were prepared by substantially the same methodology described in Examples 1–3, with the exception of employing the products of preparations 15 and 17 in the reactions.

TABLE 2

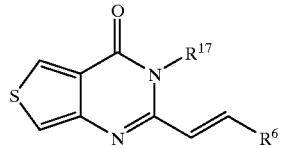

| R[6] | R[17] | Physical Data |
|---|---|---|
| 2-fluorophenyl | 2-methylphenyl | mp 195° C.<br>$^1$H NMR δ 8.31(d, J=3.2Hz, 1H), 7.94(d, J=15.9Hz, 1H), 7.62(d, J=3.3Hz, 1H), 7.43–7.33(m, 3H), 7.23–7.16 (m, 3H), 7.05–6.85(m, 2H), 6.38(d, J=16.1Hz, 1H), 2.12(s, 3H)<br>Analysis calculated for $C_{21}H_{15}FN_2OS$: C, 69.61; H, 4.14; N, 7.73. Found: C, 69.11; H, 4.10; N, 7.35. |
| pyrid-2-yl | 2-methylphenyl | mp 190–191° C.<br>$^1$H NMR δ 8.46(dd, J=1.6, 4.5Hz, 1H), 8.31(d, J=3.2 Hz, 1H), 7.83(d, J=15.3Hz, 1H), 7.61–7.56(m, 2H), 7.42–7.35(m, 3H), 7.24–7.11(m, 3H), 6.83(d, J=15.2Hz, 1H), 2.11(s, 3H)<br>Analysis calculated for $C_{20}H_{15}N_3OS$: C, 69.57; H, 4.35; N, 12.17. Found: C, 69.16; H, 4.36; N, 11.76. |
| pyrid-2-yl | 2-chlorophenyl | mp 207° C.<br>$^1$H NMR δ 8.46(dd, J=1.5, 3 Hz, 1H), 8.31(d, J=3.9Hz, 1H), 7.83(d, J=14.8Hz, 1H), 7.62–7.12(m, 8H), 6.85 (d, J=14.8Hz, 1H) |

EXAMPLE 6

2-[2-(2-Fluoro-phenyl)-vinyl]-3-o-tolyl-3H-pteridin-4-one

A mixture of fused zinc chloride (0.17 g, 1.25 mmol), dioxane (15 mL), 2-methyl-3-(2-methyl-phenyl)-3H-pteridin-4-one (0.174 g, 0.69 mmol, preparation 8), and 2-fluorobenzaldehyde (0.22 mL, 2.07 mmol), and acetic anhydride 0.195 mL, 2.07 mmol) was refluxed overnight. The reaction was cooled and concentrated. The residual material was partitioned between saturated aqueous sodium bicarbonate and methylene chloride. The layers were carefully shaken and separated. The organic layer was washed with brine, dried and concentrated. The residue was flash chromatographed on silica gel (0.75×4 inches) with elution proceeding as follows: 50% ethyl acetate/hexane (300 mL), forerun; 60% ethyl acetate/hexane (400 mL). 2-[2-(2-Fluoro-phenyl)-vinyl]-3-o-tolyl-3H-pteridin-4-one (0.137 g, 55%) was isolated as a yellow crystalline solid. A sample was recrystallized from ethyl acetate.

Mp >250° C.; $^1$H NMR δ8.98 (d, J=2 Hz, 1 H), 8.80 (d, J=2 Hz, 1 H), 8.36 (d, J=15.5 Hz, 1 H), 7.54–7.40 (m, 3 H), 7.35–7.20 (m, 3 H), 7.15–6.98 (m, 2 H), 6.49 (d, J=15 Hz, 1 H), 2.15 (s, 3 H). Analysis calculated for $C_{21}H_{15}FN_4O$: C, 70.38; H, 4.22; N, 15.63. Found: C, 70.07; H, 4.21; N, 15.78.

EXAMPLE 7

The compounds in Table 3 were prepared following substantially the same procedure as found in Example 6 starting with the product of either preparation 8 or preparation 11.

TABLE 3

| R⁶ | R¹⁷ | Physical Data |
|---|---|---|
| pyrid-2-yl | 2-methylphenyl | mp > 250° C.<br>¹H NMR δ 9.00(d, J=2Hz, 1H), 8.83(d, J=2Hz, 1H), 8.51(long range coupled d, J=3.5Hz, 1H), 8.29(d, J=15 Hz, 1H), 7.68(dt, J=2, 7.5 Hz, 1H), 7.56–7.40(m, 3H), 7.35(d, J=7.5Hz, 1H), 7.26–7.18(m, 2H), 7.01(d, J=15Hz, 1H), 2.18(s, 3H)<br>Analysis calculated for $C_{20}H_{15}N_5O$: C, 70.37; H, 4.43; N, 20.52. Found: C, 69.97; H, 4.43; N, 20.78. |
| 2-fluorophenyl | 2-chlorophenyl | mp 228–230° C.<br>¹H NMR δ 8.98(d, J=2Hz, 1H), 8.81(d, J=2Hz, 1H), 8.35(d, J=15.5Hz, 1H), 7.71–7.63(m, 1H), 7.55(sym m, 2H), 7.48–7.40(m, 1H), 7.37–7.25(m, 2H), 7.13–6.95 (m, 2H), 6.47(dd, J=1, 15.5 Hz, 1H).<br>Analysis calculated for $C_{20}H_{12}ClFN_4O \cdot 0.5H_2O$: C, 61.94; H, 3.38; N, 14.45. Found: C, 62.17; H, 3.32; N, 14.54. |
| pyrid-2-yl | 2-chlorophenyl | mp 231–232° C.<br>¹H NMR δ 8.98(d, J=2Hz, 1H), 8.81(d, J=2Hz, 1H), 8.51–8.48(sym m, 1H), 8.28 (d, J=15Hz, 1H), 7.72–7.62 (m, 2H), 7.55(sym m, 2H), 7.48–7.40(m, 1H), 7.34(d, J=7.5Hz, 1H), 7.19(sym m, 1H), 6.98(d, J=15Hz, 1H)<br>Analysis calculated for $C_{19}H_{12}ClN_5O \cdot 0.5H_2O$: C, 61.55; H, 3.53; N, 18.89. Found: C, 61.67; H, 3.38; N, 19.13. |

EXAMPLE 8

2-[2-(2-Fluoro-phenyl)-vinyl]-3-o-tolyl-3H-pyrido [3,4-d]pyrimidin-4-one

The title compound was prepared according to the procedures of Examples 1–3 from the product of preparation 20.

Mp 211–211.5° C.; ¹H NMR δ9.26 (s, 1 H), 8.70 (d, J=5 Hz, 1 h), 8.18 (d, J=15.5 Hz, 1 H), 8.08 (d, J=4.5 Hz, 1 H), 7.54–7.48 (m, 3 h), 7.46–7.15 (m, 3 H), 7.13–7.00 (m, 2 h), 647 (d, J=15.5 Hz, 1 H), 2.13 (s, 3 H). Analysis calculated for $C_{22}H_{16}FN_3O \cdot 0.125 H_2O$: C, 73.47; H, 4.55; N, 11.68. Found: C, 73.35; H, 4.49; N, 11.66.

EXAMPLE 9

3-(2-Chloro-phenyl)-2-(2-pyridin-2-yl-ethyl)-3H-thieno[3,2-d]pyrimidin-4-one Hydrochloride A mixture of 3-(2-chloro-phenyl)-2-[2-pyrid-2-yl-vinyl]-3H-thieno[3,2-d]pyrimidin-4-one (0.12 g, 0.33 mmol), ethanol, 10 mL), formic acid (0.55 mL, 14.8 mmol) and 10% palladium on carbon (0.12 g) was refluxed 4 hours, cooled and diluted with ethanol and water. The mixture was filtered through Celite® (trademark) and the pad was rinsed with ethyl acetate and water. The filtrate was treated with saturated aqueous sodium bicarbonate and the phases were separated. The aqueous layer was extracted with ethyl acetate and the combined organic phase was washed with water and brine, dried over sodium sulfate, and concentrated to afford 0.094 g of 3-(2-chloro-phenyl)-2-(2-pyridin-2-yl-ethyl)-3H-thieno[3,2-d]pyrimidin-4-one as a tan film. The material was dissolved in dioxane (3 mL) and treated with ether saturated with hydrogen chloride. The solid was collected and weighed 0.094 g. The solid was taken up in water, concentrated, and azeotropically dried by suspending the product in chloroform and concentrating three times to yield 3-(2-chloro-phenyl)-2-(2-pyridin-2-yl-ethyl)-3H-thieno[3, 2-d]pyrimidin-4-one hydrochloride (0.038 g, 31%) as a yellow solid.

Mp 136° C. Analysis calculated for $C_{19}H_{14}ClN_3OS$ HCl 1.5 $H_2O$: C, 52.13; H, 4.11; N, 9.15. Found: C, 51.96; H, 3.78; N, 9.27.

EXAMPLE 10

The compounds in Table 4 were prepared following the procedure of Example 9.

TABLE 4

| R⁶ | R¹⁷ | Physical Data |
|---|---|---|
| 2-fluorophenyl | 2-methylphenyl | mp 168° C.<br>¹H NMR δ 7.80(d, J=5.3Hz, 1H), 7.38–7.31(m, 4H), 7.05–6.92(m, 6H), 3.07(t, J=7.9 Hz, 2H), 2.62(sym m, 2H), 2.04(s, 3H)<br>MS m/e = 364 |
| pyrid-2-yl | 2-methylphenyl | mp 190–191° C.<br>¹H NMR δ 8.41(d, J=4.3Hz, 1H), 7.75(d, J=5.3Hz, 1H), 7.49(dt, J=1.6, 7.6Hz, 1H), 7.36–7.24(m, 4H), 7.12–7.00 (m, 3H), 3.27–3.21(m, 2H), 2.83–2.73(m, 2H), 2.05(s, 3H) |
| 4-methyl-1,3-thiazol-2-yl | 2-methylphenyl | Isolated as a foam<br>¹H NMR δ 7.78.(d, J=5.4Hz, 1H), 7.34(m, 4H), 7.07(d, J=7.3Hz, 1H), 6.64(s, 1H), 3.44(sym m, 2H), 2.83(m, 1H), 2.67(m, 1H), 2.33(s, 3H), 2.05(s, 3H). The HCl salt was precipitated from 1 N ethereal HCl and had: mp 146–150° C. |
| 2-methyl-1,3-thiazol-4-yl | 2-methylphenyl | Isolated as a yellow film<br>¹H NMR δ 7.79(dd, J=1.2, 5.3Hz, 1H), 7.36(m, 4H), 7.05(d, J=7.4Hz, 1H), 6.67(s, 1H), 3.18(t with incompletely resolved fine coupling, J=8.1 |

TABLE 4-continued

[Structure: thieno-pyrimidinone with R17 on N and R6 on ethyl chain]

| R6 | R17 | Physical Data |
|---|---|---|
| | | Hz, 2H), 2.74(m, 1H), 2.65 (m, 1H), 2.60(s, 3H), 2.03(s, 3H). The HCl salt was precipitated from 1 N ethereal HCl and had: mp 127–129° C. |

EXAMPLE 11

The compounds in Table 5 were prepared following the procedure of Example 9.

TABLE 5

[Structure: thieno-pyrimidinone with R17 on N and R6 on ethyl chain]

| R6 | R17 | Physical Data |
|---|---|---|
| pyrid-2-yl | 2-methylphenyl | Hydrochloride mp 162° C. $^1$H NMR (DMSO $d_6$) δ 8.76(d, J=4.9Hz, 1H), 8.54(d, J=3.2Hz, 1H), 8.45(dt, J=1.5, 8Hz, 1H), 7.96(d, J=7.9 Hz, 1H), 7.85(t, J=7Hz, 1H), 7.81(d, J=3.2Hz, 1H), 7.44–7.37(m, 4H), 3.42(t, J=6.9Hz, 2H), 2.86(dt, J=6.8, 18Hz, 1H), 2.60(dt, J=6.8, 18Hz, 1H), 2.03(s, 3H) Analysis calculated for $C_{20}H_{17}N_3OS \cdot HCl \cdot H_2O$: C, 59.85; H, 4.90; N, 10.00. Found: C, 59.58; H, 4.99; N, 9.88. |
| pyrid-2-yl | 2-chlorophenyl | Hydrochloride mp 181–183° C. $^1$H NMR (DMSO $d_6$) δ 8.77(d, J=4.8Hz, 1H), 8.57(d, J=3.2Hz, 1H), 8.46(dt, J=1.5, 8Hz, 1H), 7.98(d, J=8 Hz, 1H), 7.86(t, J=6.5Hz, 1H), 7.76–7.68(m, 2H), 7.60–7.56(m, 2H), 3.45(t, J=7 Hz, 2H), 2.93(dt, J=6.7, 18 Hz, 1H), 2.63(dt, J=6.7, 18 Hz, 1H) Analysis calculated for $C_{19}H_{14}ClN_3OS \cdot HCl \cdot 1.5H_2O$: C, 53.46; H, 4.10; N, 9.85. Found: C, 53.64; H, 3.95; N, 9.48. |

EXAMPLE 12

5-(2-Pyridin-2-yl-vinyl)-6-o-tolyl-3,6-dihydro-[1,2,3]triazolo[4,5-d]pyrimidin-7-one To a mixture of fused zinc chloride (0.551 g, 4.04 mmol) and dioxane (20 mL) was added 5-methyl-6-o-tolyl-3,6-dihydro-[1,2,3]triazolo[4,5-d]pyrimidin-7-one (0.488 g, 2.02 mmol),2-pyridinecarboxaldehyde (0.58 mL, 6.06 mmol), and acetic anhydride (0.57 mL, 6.06 mmol). The mixture was heated to 70° C. for 6 hours, cooled, and quenched with saturated sodium bicarbonate. This mixture was stirred overnight at ambient temperature. The dioxane was removed at reduced pressure and the resulting black liquid was extracted with methylene chloride. The organic phase was dried over magnesium sulfate, treated with activated carbon, filtered, and concentrated. The residue (1.5 g) was flash chromatographed on silica gel (50 g). Elution with 50% and 60% ethyl acetate/hexane gave 5-(2-pyridin-2-yl-vinyl)-6-o-tolyl-3,6-dihydro-[1,2,3]triazolo[4,5-d]pyrimidin-7-one (0.023 g, 3.5%).

$^1$H NMR δ9.06 (d, J=7.3 Hz, 1 H), 8.70 (m, 2 H), 7.60 (t, J=7.8 Hz, 1 H), 7.50 (t, J=7.7 Hz, 1 H), 7.32–7.00 (m, 4 H), 6.80 (t, J=8.2 Hz, 1 H), 6.59 (t, J=8 Hz, 1 H), 2.28 (s, 3 H); MS m/e=330. The product was treated with hydrogen chloride (HCl) in dioxane to form the hydrochloride salt which had a melting point (mp) of 80–85° C.

Preparation 1

3-Acetamidothiophene-2-carboxylic acid

To a solution of methyl 3-aminothiophene-2carboxylate (10 g, 0.0637 mol) and triethylamine (10.3 g, 0.102 mol) in methylene chloride was added acetyl chloride (8.0 g, 0.102 mol in 10 mL of methylene chloride), dropwise. The reaction was stirred 3 hours at ambient temperature. The mixture was quenched with water and the phases were separated. The aqueous layer was extracted twice with methylene chloride and the combined organic phase was washed with water and brine, dried over sodium sulfate and concentrated to afford 14.0 g of yellow solid product which was suitable for reaction without further purification.

$^1$H NMR δ8.10 (d, J=5.4 Hz, 1 H), 7.43 (d,J=5.4 Hz, 1 H), 3.86 (s, 1 H), 2.20 (s, 3 H); MS m/e=199.

The product was added to 200 mL of 10% methanolic potassium hydroxide and heated to 60–65° C. for 4 hours. The reaction was concentrated and the residue taken up in water. The aqueous solution was extracted with ether and then made acidic with 6 N hydrochloric acid (HCl). The precipitate was filtered, washed well with water, and air dried to yield 9.5 g (80%) of 3-acetamidothiophene-2-carboxylic acid as a tan solid.

Mp 212–213° C.; $^1$H NMR (DMSO $d_6$) δ7.82 (d, J=5.4 Hz, 1 H), 7.72 (d, J=5.4 Hz, 1 H), 2.06 (s, 3 H).

Preparation 2

2-Methyl-3-(2-methylphenyl)-3H-thieno[3,2-d]pyrimidin-4-one

To a mixture of 3-acetamidothiophene-2-carboxylic acid (15.1 g, 75.67 mmol) and sodium acetate (6.45 g, 78.6 mmol) in dioxane (200 mL) was added acetic anhydride (71 mL, 75.7 mmol). The reaction was refluxed 2 hours, cooled to ambient temperature and partitioned between chloroform and water. Phases were separated and the aqueous layer was extracted with chloroform. The combined organic phase was washed with water and brine, dried over magnesiuym sulfate and concentrated to leave 15.1 g of 2-methyl-thieno[3,2-d][1,3]oxazin-4-one as a brown oil which slowly solidified.

$^1$H NMR δ7.78 (d, J=6.5 Hz, 1 H), 7.14 (d, J=6.5 Hz, 1 H), 2.40 (s, 3H); MS m/e=167. The material was used without further purification.

2-Methyl-thieno[3,2-d][1,3]oxazin-4-one (12.7 g, 76 mmol) and o-toluidine (16.2 mL, 152 mmol) were combined in acetic acid (175 mL) and refluxed for 3 hours. The reaction was concentrated and the residue was partitioned between ethyl acetate and water. The two phase mixture was treated with sodium bicarbonate until the aqueous layer was basic and the phases were then separated. The aqueous phase was extracted with ethyl acetate and the combined organic layer was washed with water and brine, dried over sodium sulfate and concentrated to leave a black oil. This residue was purified by flash chromatography on silica gel (60×200 mm). Elution with 20% ethyl acetate/hexane gave 16.2 g of impure product and 3 g of uncyclized diamide biproduct. The impure product was chromatographed a second time as above but with 10% and 15% ethyl acetate/hexane elution. In this fashion 9.2 g (47%) of 2-methyl-3-(2-methylphenyl)-3H-thieno[3,2-d]pyrimidin-4-one was isolated as a light yellow solid. $^1$H NMR δ7.70 (d, J=5.3 Hz, 1 H), 7.39–7.30 (m, 3 H), 7.29 (d, J=5.3 Hz, 1 H), 7.13 (d, J=7.8 Hz, 1 H), 2.15 (s, 3 H), 2.10 (s, 3 H).

Preparation 3

2-Methyl-3-(2-chlorophenyl)-3H-thieno[3,2-d]pyrimidin-4-one

2-Methyl-thieno[3,2-d][1,3]oxazin-4-one (1.67 g, 10 mmol) and o-chloroaniline (2.1 mL, 20 mmol) were combined in acetic acid (20 mL) and refluxed for 4.5 hours. The reaction was partitioned between ethyl acetate and water. The two phase mixture was treated with sodium bicarbonate until the aqueous layer was basic and the phases were then separated. The aqueous phase was extracted with ethyl acetate and the combined organic layer was washed with water and brine, dried over sodium sulfate and concentrated to leave a brown oil. This residue was purified by flash chromatography on silica gel (30×150 mm). Elution with 10% and 20% ethyl acetate/hexane gave 1.42 g (51%) of 2-methyl-3-(2-chlorophenyl)-3H-thieno[3,2-d]pyrimidin-4-one was isolated as a brown oil which solidified on standing.

MP 118–121° C.; $^1$H NMR δ7.78 (d, J=5.3 Hz, 1 H), 7.57 (m, 1 H), 7.46–7.43 (m, 2 H), 7.33–7.29 (m, 2 H), 2.20 (s, 3 H); MS m/e=276.

Preparation 4

2-Methyl-3-(2-chloropyrid-3-yl)-3H-thieno[3,2-d]pyrimidin-4-one

To a mixture of pyridine (4 mL), 3-amino-2-chloropyridine (0.514 g, 4 mmol), and 3-acetamidothiophene-2-carboxylic acid (0.370 g, 4 mmol) was added phosphorus trichloride (0.02 mL, 2.3 mmol). The reaction was heated to 105° C. for 3 hours, cooled to ambient temperature and partitioned between ethyl acetate and water. Phases were separated and the aqueous layer was extracted with ethyl acetate. The combined organic phase was washed with water and brine, dried over sodium sulfate and concentrated to a greenish brown oil. This residue was flash chromatographed on silica gel (20×120 mm) eluting with 20–40% ethyl acetate/hexane to afford 0.350 g (63%) of 2-methyl-3-(2-chloropyrid-3-yl)-3H-thieno[3,2-d]pyrimidin-4-one as a yellow foam.

$^1$H NMR δ8.58–8.56 (m, 1 H), 7.83 (d, J=5.2 Hz, 1 H), 7.74–7.71 (m, 1 H), 7.50–7.46 (m, 1 H), 7.33 (d, J=5.3 Hz, 1 H), 2.24 (s, 3 H); MS m/e=277.

Preparation 5

2-Methyl-3-(2-bromophenyl)-3H-thieno[3,2-d]pyrimidin-4-one

To a mixture of pyridine (6 mL), 2-bromoaniline (1.03 g, 6 mmol), and 3-acetamidothiophene-2-carboxylic acid (0.555 g, 3 mmol) was added phosphorus trichloride (0.03 mL, 3.45 mmol). The reaction was heated to 105° C. for 4 hours, cooled to ambient temperature and partitioned between chloroform and water (an insoluble precipitate was removed by filtration). Phases were separated and the aqueous layer was extracted with chloroform. The combined organic phase was washed with water and brine, dried over magnesium sulfate and concentrated to a dull yellow film. This residue was flash chromatographed on silica gel (30×125 mm) eluting with 15–25% ethyl acetate/hexane to afford 0.411 g (47%) of 2-methyl-3-(2-bromophenyl)-3H-thieno[3,2-d]pyrimidin-4-one as a yellow foam, $^1$H NMR δ7.76–7.55 (m, 2 H), 7.44 (t, J=7.2 Hz, 1 H), 7.39–7.05 (m, 3 H), 2.10 (s, 3 H); MS m/e=320 and 322.

Preparation 6

3-Aminopyrazine-2-carboxylic acid o-toluamide

A mixture of 3-aminopyrazine carboxylic acid (5.0 g, 35.94 mmol), methylene chloride (110 mL), 4-dimethylaminopyridine (10.98 g, 89.85 mmol), o-toluidine (4.22 mL, 39.53 mmol), and 1-(3-dimethylaminopropyl)-3-ethylcarbodiimide hydrochloride (8.27 g, 43.13 mmol) was stirred overnight at ambient temperature. The solvent was removed and the residue was diluted with ethyl acetate. This organic phase was extracted with 1N lithium chloride (LiCl), water, and brine, dried over calcium sulfate and concentrated. The residue was flash chromatographed on silica gel (2.75×4 inches) with elution proceeding as follows: hexane (300 mL), nil; 20% ethyl acetate/hexane (500 mL), unweighed recovered o-toluidine; 20% ethyl acetate/hexane (1000 mL) and 30% ethyl acetate/hexane (2000 mL), 4.79 g (58%) of 3-aminopyrazine-2-carboxylic acid o-toluamide as a yellow crystalline solid.

Mp 135–137° C.; $^1$H NMR δ9.80 (br s, 1 H), 8.22 (d, J=2.5 Hz, 1 H), 8.11 (d, J=8.0 Hz, 1 H), 7.87 (d, J=2.5 Hz, 1 H), 7.33–7.23 (m, 2 H), 7.10 (dt, J=1, 7.5 Hz, 1 H), 2.39 (s, 3 H).

Preparation 7

3-Acetamidopyrazine-2-carboxylic acid o-toluamide

A mixture of 3-aminopyrazine-2carboxylic acid o-toluamide (1.0 g, 4.39 mmol) and acetic anhydride (12 mL) was refluxed 2 hours. The solvent was removed and the residue was triturated with hot ethyl acetate. The ethyl acetate slurry was cooled and the product was collected and rinsed with ether to afford 0.893 g (76%) of 3-acetamidopyrazine-2-carboxylic acid o-toluamide.

$^1$H NMR δ11.88 (br s, 1 H), 10.0 (br s, 1 H), 8.65 (d, J=2.5 Hz, 1 H), 8.28 (d, J=2.5 Hz, 1 H), 8.04 (d, J=8 Hz, 1 H), 7.38–7.24 (m, 2 H), 7.20–7.11 (m, 1 H), 2.39 (s, 3 H), 2.38 (s, 3 H). The material was used without further purification.

Preparation 8

2-Methyl-3-(2-methyl-phenyl)-3H-pteridin-4-one

To a mixture of 3-acetamidopyrazine-2-carboxylic acid o-toluamide (1.0 g, 3.70 mmol), triphenylphosphine (2.91 g, 11.1 mmol), and 4-dimethylaminopyridine (0.045 g, about 10 mol %) in dioxane (45 mL) was added diethyl azodicarboxylate (1.75 mL, 11.1 mmol) dropwise via syringe. The reaction was refluxed overnight, cooled to ambient temperature and concentrated. The residue was partitioned between methylene chloride and water. The phases were separated and the organic layer was washed with brine, dried and concentrated. The residue was flash chromatographed on silica gel (2.25×4 inches, packed in hexane) with elution proceeding as follows: 20%–80% ethyl acetate/hexane, forerun; 85% ethyl acetate/hexane (1000 mL), 0.71 g (76%) of 2-methyl-3-(2-methyl-phenyl)-3H-pteridin-4-one which was suitable for use without further purification. A sample was recrystallized from ethyl acetate.

Mp 186–187° C.; $^1$H NMR δ8.98 (d, J=2 Hz, 1 H), 8.83 (d, J=2 Hz, 1 H), 7.51–7.35 (m, 3 H), 7.18 (d, J=7 Hz, 1 H), 2.30 (s, 3 H), 2.16 (s, 3 H).

Preparation 9

3-Aminopyrazine-2-carboxylic acid 2-chlorophenylamide

A mixture of 3-aminopyrazine carboxylic acid (7.0 g, 50.32 mmol), methylene chloride (60 mL), dimethylformamide (40 mL), 4-dimethylaminopyridine (15.37 g, 126 mmol), 2-chloroaniline (5.82 mL, 55.35 mmol), and 1-(3-dimethylaminopropyl)-3-ethylcarbodiimide hydrochloride (11.58 g, 60.38 mmol) was stirred overnight at ambient temperature. The solvent was removed and the residue was mixed with ethyl acetate and 1 N lithium chloride. The precipitate which formed was filtered and rinsed with 1 N lithium chloride, ethyl acetate, and ether and then air dried to afford 6.22 g (50%) of 3-aminopyrazine-2-carboxylic acid 2-chlorophenylamide as fluffy yellow crystals.

Mp 177–179° C.; $^1$H NMR δ10.47 (br s, 1 H), 8.52 (dd, J=1.5, 8.5 Hz, 1 H), 8.23 (d, J=2.5 Hz, 1 H), 7.92 (d, J=2.5 Hz, 1 H), 7.43 (dd, J=1.5, 8 Hz, 1 H), 7.33 (dt, J=1.5, 7.5 Hz, 1 H), 7.09 (dt, J=1.5, 7.5 Hz, 1 H).

Preparation 10

3-Acetamidopyrazine-2-carboxylic acid 2-chlorophenylamide

A mixture of 3-aminopyrazine-2-carboxylic acid 2-chlorophenyl (4.0 g, 16.1 mmol) and acetic anhydride (25 mL) was refluxed for 2 hours. The solvent was removed and the residue was partitioned between methylene chloride and saturated aqueous sodium bicarbonate. The phases were separated and the organic layer was washed with brine, dried and concentrated. The residue was flash chromatographed on silica gel (2.25×4 inches) with elution proceeding as follows: hexane (200 mL) and 25% ethyl acetate/hexane (500 mL), forerun; 40% ethyl acetate/hexane (700 mL, 0.69 g of an unidentified material; 40% ethyl acetate/hexane (200 mL) and 60% ethyl acetate/hexane (500 mL), 0.836 g (18%) of 3-acetamidopyrazine-2-carboxylic acid 2-chlorophenylamide.

Mp 194–196° C.; $^1$H NMR δ11.70 (br s, 1 H), 10.65 (br s, 1 H), 8.66 (d, J=2.5 Hz, 1H), 8.49 (dd, J=1.5, 8 Hz, 1 H), 8.31 (d, J=2.5 Hz, 1 H), 7.46 (dd, J=1.5, 10 Hz, 1 H), 7.36 (dt, J=1.5, 9 Hz, 1 H), 7.14 (dt, J=1.5, 7.5 Hz, 1 H), 2.42 (s, 3 H). The material was used without further purification.

Preparation 11

2-Methyl-3-(2-chloro-phenyl)-3H-pteridin-4-one

To a mixture of 3-acetamidopyrazine-2-carboxylic acid 2-chlorophenylamide (0.816 g, 2.81 mmol), triphenylphosphine (2.21 g, 8.43 mmol), and 4-dimethylaminopyridine (0.034 g, 0.28 mmol) in dioxane (35 mL) was added diethyl azodicarboxylate (1.33 mL, 8.43 mmol), dropwise via syringe. The reaction was refluxed overnight, cooled to ambient temperature and concentrated. The residue was partitioned between methylene chloride and water. The phases were separated and the organic layer was washed with brine, dried and concentrated. The residue was flash chromatographed on silica gel (1.5×5 inches, packed in hexane) with elution proceeding as follows: 20% ethyl acetate/hexane (250 mL), forerun; 40% ethyl acetate/hexane (1600 mL), unweighed triphenylphosphine oxide; 60% ethyl acetate/hexane (500 mL) and 75% ethyl acetate/hexane (500 mL), nil; 80% ethyl acetate/hexane (1000 mL), 0.62 g (81%) of 2-methyl-3-(2-chloro-phenyl)-3H-pteridin-4-one as a brown foam which was suitable for use without further purification. A sample was triturated with hexane.

MP 74–80° C.; $^1$H NMR δ8.98 (d, J=2 Hz, 1 H), 8.84 (d, J=2 Hz, 1 H), 7.70–763 (m, 1 H), 7.53 (sym m, 2 H), 7.42–7.33 (m, 1 H), 2.34 (s, 3 H).

Preparation 12

Methyl 3-acetamidothiophene-4-carboxylate

A mixture of methyl 3-aminothiophene-4-carboxylate hydrochloride (3.1 g, 16 mmol) and triethylamine (6.7 mL, 48 mmol), in methylene chloride (75 mL) was stirred 30 minutes and then chilled over wet ice. Acetyl chloride (1.4 mL, 19.2 mmol) was added and the reaction was warmed to ambient temperature and stirred 1 hour. The reaction was quenched with water and diluted with methylene chloride. The phases were separated and the aqueous layer was extracted with methylene chloride. The combined organic layer was washed with water, dried over magnesium sulfate, and concentrated to afford 2.85 g (91%) of methyl 3-acetamidothiophene-4-carboxylate as a brown oil which solidified on standing. The product was suitable for use without purification.

$^1$H NMR δ7.98 (d, 2 H), 3.87 (s, 3 H), 2.18 (s, 3 H).

Preparation 13

3-Acetamidothiophene-4-carboxylic acid

Methyl 3-acetamidothiophene-4-carboxylate (10.0 g, 50.25 mmol) was added to a 5% methanolic potassium hydroxide solution (100 mL). The mixture was refluxed 2 hours, cooled, and concentrated. The residue was dissolved in water and the acidity was adjusted to pH 1 by addition of 1 N hydrochloric acid (HCl). The precipitate was collected, washed with water, and air dried to afford 8.66 g (93%) of 3-acetamidothiophene-4-carboxylic acid.

Mp 206° C.; $^1$H NMR δ8.29 (d, 1 H), 7.88 (d, 1 H), 2.11 (s, 3 H). The product was used without purification.

Preparation 14

2-Methyl-thieno[3,4-d][1,3]oxazin-4-one

A mixture of 3-acetamidothiophene-4-carboxylic acid (1.6 g, 8.65 mmol), dioxane (40 mL), acetic anhydride (10.2 mL, 86.5 mmol), and sodium acetate (0.75 g, 9.08 mmol) was refluxed overnight. The reaction was cooled and concentrated. The residue was partitioned between ethyl acetate and water. Phases were separated and the aqueous layer was extracted with ethyl acetate. The combined organic layer was washed with water and brine, dried over sodium sulfate, and concentrated to afford 1.39 g (96%) of 2-methyl-thieno [3,4-d][1,3]oxazin-4-one as a tan solid.

$^1$H NMR δ8.34 (d, J=3.4 Hz, 1 H), 7.40 D, J=3.4 Hz, 1 H), 2.38 (s, 3 H). The product was suitable for use without purification.

Preparation 15

2-Methyl-3-o-tolyl-3H-thieno[3,4]pyrimidin-4-one

To a slurry of 2-methyl-thieno[3,4-d][1,3]oxazin-4-one (1.0 g, 5.99 mmol) and acetic acid (15 mL) was added o-toluidine (1.2 mL, 10.78 mmol). The mixture was refluxed 3 hours, cooled, and concentrated. The residue was partitioned between ethyl acetate and water and the aqueous phase was made basic by careful addition of saturated aqueous sodium bicarbonate. The phases were separated and the aqueous layer was extracted with ethyl acetate. The combined organic layer was washed with water and brine, dried over sodium sulfate and concentrated to a black oil. The oil was flash chromatographed on silica gel (30×100 mm) eluting with 20% ethyl acetate/hexane. Product fractions were combined to afford 0.303 g of 2-methyl-3-o-tolyl-3H-thieno[3,4-d]pyrimidin-4-one as a tan oil which solidified on standing.

Mp 122–123° C.; $^1$H NMR δ8.25 (d, J=3.2 Hz, 1 H), 7.47 (d, J=3.3 Hz, 1 H), 7.37–7.32 (m, 3 H), 7.12 (d, J=6.8 Hz, 1 H), 2.13 (s, 3 H), 2.10 (s, 3 H).

Mixed fractions were chromatographed a second time. Product fractions from this purification were combined, concentrated and the residues were triturated with 10% ethyl acetate/hexane to afford an additional 0.447 g of product. In this fashion 0.75 g (49%) of product was obtained. Later fractions from the chromatography contained uncyclized diamide by product which could be cyclized according the procedure of preparation 17.

Preparation 16

3-Acetamidothiophene-4-carboxylic acid 2-chlorophenylamide

To a slurry of 2-methyl-thieno[3,4-d][1,3]oxazin-4-one (1.3 g, 7.78 mmol) and acetic acid (15 mL) was added 2-chloroaniline (1.64 mL, 15.57 mmol). The mixture was refluxed 4 hours, cooled, and concentrated. The residue was partitioned between ethyl acetate and water and the aqueous phase was made basic by careful addition of saturated aqueous sodium bicarbonate. The phases were separated and the aqueous layer was extracted with ethyl acetate. The combined organic layer was washed with water and brine, dried over sodium sulfate and concentrated to a black oil. The oil was flash chromatographed on silica gel (30×100 mm) eluting with 10% ethyl acetate/hexane. The first component eluting from the column, 0.363 g of white solid was identified as 3-acetamidothiophene-4-carboxylic acid 2-chlorophenylamide.

$^1$H NMR δ8.33 (d, J=9.7 Hz, 1 H), 8.28 (d, J=3.4 Hz, 1 H), 8.23 (br s, 1 H), 7.78 (d, J=3.3 Hz, 1 H), 7.44–7.41 (m, 1 h), 7.30–7.24 (m, 1 H), 7.14–7.11 (m, 1 H), 2.19 (s, 3 H); MS m/e=294.

Continued elution gave 0.273 g of an unidentified white solid which had $^1$H NMR δ8.36 (d, J=8.3 Hz, 1 h), 7.56 (br s, 1 h), 7.35–7.33 (m, 1 h), 7.28–7.22 (m, 1 H), 7.04–6.99 (m, 1 H), 2.22 (s, 3 H).

Preparation 17

2-Methyl-3-(2-chloro-phenyl)-3H-thieno[3,4-d]pyrimidin-4-one

A mixture of 3-acetamidothiophene-4carboxylic acid 2-chlorophenylamide (0.36 g, 1.23 mmol), toluene (15 mL), and phosphorous oxychloride (0.35 mL, 3.7 mmol) was refluxed 8 hours with azeotropic removal of water (Dean-Stark apparatus). The reaction was cooled and partitioned between ethyl acetate and water. The phases were separated and the aqueous layer was extracted with ethyl acetate. The combined organic layer was washed with water and brine, dried over sodium sulfate, and concentrated. The residue was flash chromatographed on silica gel (20×85 mm) eluting with 10% ethyl acetate/hexane. After an unweighed forerun, 2-methyl-3-(2-chloro-phenyl)-3H-thieno[3,4-d]pyrimidin-4-one was isolated as an off white solid.

$^1$H NMR δ8.28–8.26 (m, 1 H), 7.56–7.55 (m, 1 H), 7.49–7.40 (m, 3 H), 7.31 (m, 1 H), 2.10 (s, 3 H); MS m/e=277.

Preparation 18

3-Aminopyridine-4-carboxylic acid

To an ice cold mixture of 3,4-pyridinedicarboximide (5.2 g, 35.11 mmol) in 10% sodium hydroxide (85 mL) was added bromine (1.84 mL, 35.8 mmol), dropwise. The resulting solution was heated to 80° C. for 1 hour, cooled on ice, and the acidity was carefully adjusted to pH 5.5 with acetic acid. The precipitate was collected, washed well with water and air dried to afford 3-aminopyridine-4-carboxylic acid (2.74 g, 57%).

$^1$H NMR (DMSO d$_6$) δ8.20 (s,1 H), 7.72 (d, J=5 Hz, 1 H), 7.45 (d, J=5 Hz, 1 H). The material was used without purification.

Preparation 19

2-Methyl-3-oxa-1,7-diaza-naphthalen-4-one

A mixture of 3-aminopyridine-4-carboxylic acid (3.38 g, 24.5 mmol), acetic anhydride (15 mL), and sulfuric acid (3 drops) was refluxed 4 hours. The reaction was cooled and carefully quenched with solid sodium bicarbonate. The mixture was filtered through Celite® (trademark). The filtrate was extracted with ethyl acetate. This organic phase was washed with brine, dried over magnesium sulfate and concentrated to give 2-methyl-3-oxa-1,7-diaza-naphthalen-4-one (1.95 g, 49%) as a brown crystalline material.

$^1$H NMR δ9.00 (s, 1 H), 8.78 (d, J=5 Hz, 1 H), 7.96 (d, J=5 Hz, 1 H), 2.52 (s, 3 H). The product was suitable for use without further purification.

Preparation 20

2-Methyl-3-o-tolyl-3H-pyrido[3,4-d]pyrimidin-4-one

2-Methyl-3-oxa-1,7-diaza-naphthalen-4-one (1.95 g, 12.0 mmol) was dissolved in acetic acid (30 mL) and o-toluidine (1.92 mL. 18 mmol) was added. The reaction was refluxed 7 hours, cooled and concentrated. The residue was taken up in ethyl acetate and extracted with water, saturated aqueous sodium bicarbonate, and brine. The organic layer was dried over magnesium sulfate and concentrated. The residue was flash chromatographed on silica gel (2×4 inches, packed in hexane) with elution proceeding as follows: 10% ethyl acetate/hexane (500 mL); 25% ethyl acetate/hexane (800 mL); 25% ethyl acetate/hexane (200 mL) and 40% ethyl acetate/hexane (200 mL), unweighed recovered 2-methyl-3-oxa-1,7-diaza-naphthalen-4-one; 40% ethyl acetate/hexane (300 mL), unweighed mixed fraction; 40% ethyl acetate/hexane (3000 mL), 2-methyl-3-o-tolyl-3H-pyrido[3,4-d]pyrimidin-4-one (2.47 g, 81%) of as an off white solid.

$^1$H NMR δ9.15 (s, 1 H), 8.70 (d, J=5 Hz, 1 H), 8.05 (d, J=5 Hz, 1 H), 7.46–7.35 (m, 3 H), 7.16 (d, J=7 Hz, 1 H), 2.23

(s, 3 h), 2.13 (s, 3 H). This product was suitable for use without further purification.

Preparation 21

Cyanoacetic acid o-toluamide

A mixture of o-toluidine (5.0 mL, 47 mmol), methylene chloride (15 mL), cyanoacetic acid (8.0 g, 94 mmol), 1-hydroxybenzotriazole (12.7 g, 94 mmol), 4-dimethylaminopyridine (5 crystals, catalytic amount), and 1-(3dimethylaminopropyl)-3-ethylcarbodiimide hydrochloride (16.2 g, 94 mmol) was stirred at ambient temperature overnight. The reaction was concentrated and the residual pale yellow oil was partitioned between ethyl acetate and water. The phases were separated and the organic layer was washed with saturated sodium bicarbonate and brine, dried over sodium sulfate, and concentrated to 5.2 g of off-white solid. This solid was recrystallized from methylene chloride in two crops to afford cyanoacetic acid o-toluamide (4.71 g, 57%) as white crystals.

Mp 129–130° C.; $^1$H NMR $\delta$9.66 (s, 1 H), 8.00–7.07 (m, 6 H), 3.92 (s, 2 H), 2.20 (s, 3 H).

Preparation 22

5-Amino-1-benzyl-1,2,3-triazole-4-carboxylic acid o-toluamide

A mixture of sodium (0.598 g, 26 mmol) and ethanol (50 mL) was stirred until all the sodium had reacted to form sodium ethoxide. To this solution was added cyanoacetic acid o-toluamide (2.32 g, 13 mmol). The mixture briefly became homogeneous and yellow, then a yellow solid precipitated. At this point benzyl azide (1.73 mL, 13 mmol) was added and the reaction was stirred at ambient temperature for 17 hours. The mixture was concentrated and the yellow solid residue was slurried in water and acidified to pH 4 by addition of acetic acid. The slurry was stirred 30 minutes and the bright red solid which formed was collected and dried (5.2 g). The solid was flash chromatographed on silica gel (100 g) eluting with 0.05% ammonium hydroxide/1% methanol/methylene chloride to afford 3.5 g of impure product in two fractions. This crude product was recrystallized from 16% methanol/isopropyl ether to afford 5-amino-1-benzyl-1,2,3-triazole4carboxylic acid o-toluamide (1.52 g, 38%) as a pale orange solid.

Mp 140–144° C; $^1$H NMR $\delta$8.54 (s, 1 h), 8.00 (d, J=7.9 Hz, 1 H), 7.43–7.22 (m, 7 H), 7.07 (t, J=7.5 Hz, 1 H), 5.41 (s, 2 H), 4.86 (s, 2 H), 2.37 (s, 3 H). Concentration of the mother liquors afforded an additional 0.618 g of product.

Preparation 23

1-Benzyl-5-methyl-6-o-tolyl-3,6-dihydro-[1,2,3] triazolo[4,5-d]pyrimidin-7-one

A mixture of sodium (1.14 g, 49.5 mmol) and ethanol (100 mL) was stirred until all the sodium had reacted to form sodium ethoxide. To this solution was added 5-amino-1-benzyl-1,2,3-triazole4-carboxylic acid o-toluamide (7.6 g, 24.7 mmol) and ethyl acetate (50 mL). The reaction was refluxed 48 hours, cooled, and concentrated to an orange solid. This solid was partitioned between water and methylene chloride. The phases were separated and the organic layer was dried over magnesium sulfate. Concentration of this organic phase afforded 0.5 g of product. The aqueous layer from the extraction was acidified to pH 6.5 with acetic acid and extracted with chloroform (2×100 mL). Methanol (20 mL) was added to the chloroform to help keep the product from precipitating. This organic phase was dried over magnesium sulfate and concentrated to give 6.93 g of white crystals. The products were combined to yield 7.43 g (90%) of 1-benzyl-5-methyl-6-o-tolyl-3,6-dihydro-[1,2,3] triazolo[4,5-d]pyrimidin-7-one.

Mp 178–180° C.; $^1$H NMR (DMSO d$_6$) $\delta$9.86 (s, 1 H), 7.49–7.09 (m, 6 H), 5.49 (s, 2 H), 2.24 (s, 3 H), 2.05 (br s, 3 H).

Preparation 24

5-Methyl-6-o-tolyl-3,6-dihydro-[1,2,3]triazolo[4,5-d]pyrimidin-7-one

A mixture of 1-benzyl-5-methyl-6-o-tolyl-3,6-dihydro-[1,2,3]triazolo[4,5-d]pyrimidin-7-one (4.0 g, 12.07 mmol), acetic acid (150 mL), ethanol (25 mL), and palladium hydroxide on carbon (4.0 g) was hydrogenated on a Parr apparatus. After 5 hours the catalyst was filtered off and replaced with fresh palladium hydroxide on carbon (4.0 g). The hydrogenation was continued 48 hours longer. The reaction was filtered and the filtrate was concentrated to afford 5-methyl-6-o-tolyl-3,6-dihydro-[1,2,3]triazolo[4,5-d]pyrimidin-7one (0.488 g, 17%) as a white powder.

$^1$H NMR $\delta$9.31 (s, 1 H), 7.85 (m, 1 H), 7.30–6.95 (m, 3 H), 1.88 (s, 6 H). The product was used without purification.

Preparation 25

4-Methylthiazole-2-carboxaldehyde

A solution of 4-methylthiazole (0.91 mL, 10.0 mmol) in tetrahydrofuran (30 mL) was chilled to −78° C. and butyllithium (6.0 mL, 15 mmol, 2.5 molar solution in hexane) was added dropwise over 15 min. The pale yellow solution was stirred 1 h at −78° C. and became thick slurry. Dimethylformamide (1.2 mL, 15 mmol) was added to the reaction via syringe over 5 min. The reaction was stirred an additional 2 h at −79° C., then allowed to warm at 0° C. and poured onto wet ice. The acidity of the mixture was adjusted to pH 4 with 1 N HCl and extracted with ether. The combined ether extracts were washed with brine, dried over sodium sulfate and concentrated afford 4-methylthiazole-2-carboxaldehyde (0.734 g, 57%) as a brown oil.

$^1$H NMR $\delta$9.88 (s,1 H), 7.29 (s, 1 H), 2.50 (s, 3H). The material was used without further purification.

Preparation 26

2-Methylthiazole-4-carboxaldehyde

A solution of ethyl 2-methylthiazole-4-carboxylate (1.0 g, 5.8 mmol) in tetrahydrofuran (35 mL) was chilled to −50° C. and diisobutylaluminum hydride (12 mL, 11.97 mmol, 1 molar solution in tetrahydrofuran) was added dropwise via syringe over 15 min. The solution was stirred 30 min at −50° C., then allowed to warm to ambient temperature over 3 h. The reaciton was chilled over wet ice and carefully quenched with 10 mL of 50% methanol/tetrahydrofuran. The reaction was treated with half saturated aqueous sodium potassium tartrate (Rochelle's salt) and the mixture was filtered. The filter pad was thoroughly washed with ether and water. The entire filtrate was combined and extracted with ethyl acetate. The combined organic layer was washed with brine, dried over sodium sulfate and concentrated to 4-hyrdoxymethyl-2-methylthiazole (0.57 g, 76%) as a tan oil.

$^1$H NMR $\delta$6.97 (s, 1H), 4.54 (s, 2H), 4.43 (br s, 1H), 2.63 (2, 3H). This material was used without further purification.

An ambient temperature solution of 4-hydroxymethyl-2-methylthiazole (1.0 g, 7.75 mmol) and dichloromethane (50 mL) was treated with Dess-Martin periodinane (4.12 g, 9.69 mmol) all at once. The mixture was allowed to stir overnight. Additional periodinane (1.2 g) was added and the reaction was allowed to stir 4 hours more. The reaction was poured into 50 mL of saturated aqueous sodium thiosulfate and extracted with methylene chloride. The combined organic layer was washed with saturated aqueous sodium bicarbonate and brine, dried over sodium sulfate, and concentrated to afford 0.901 g (92%) of 2-methylthiazole-4-carboxaldehyde as an off white waxy solid which had: $^1$H NMR $\delta$9.96 (s, 1 H), 8.03 (s, 1 H), 2.77 (s, 3 H). The product was suitable for use without purification.

Preparation 27

2-Dimethylaminomethylthiazole-4-carboxaldehyde

To a slurry of 2-dimethylaminothioacetamide hydrochloride (7.7 g, 50 mmol) in ethanol (100 mL) was added ethyl bromopyruvate (6.3 mL). The mixture was refluxed 6 hours and then cooled to room temperature. More ethyl bromopyruvate (3.2 mL for a total of 75 mmol) was added and the reaction was refluxed 2.5 hours more. The mixture was cooled to ambient temperature and concentrated at reduced pressure. The residue was partitioned between water and ethyl acetate and brought to pH 10 with addition of solid potassium carbonate. The phases were separated and the aqueous layer was extracted with ethyl acetate. The combined organic phase was washed with water and brine, then it was dried over sodium sulfate and concentrated to afford an amber oil. This oil was purified by flash chromatography on silica gel (120 g). Elution proceeded as follows: 2% methanol/chloroform 200 mL, forerun; 10% methanol/chloroform, 75 mL, nil; 750 mL, 10.7 g (100%) of ethyl 2-dimethylaminomethylthiazole-4-carboxylate as a clear yellow oil. The material was suitable for use without further purification.

$^1$H NMR $\delta$8.07 (d, J=1.4 Hz, 1 H), 4.32 (q, J=7 Hz, 2 H), 3.73 (s, 2 H), 228 (s, 6 H), 1.31 (t, J=7 Hz, 3 H).

To a mixture of lithium aluminum hydride (4.5 g, 119 mmol) in ice cold tetrahydrofuran (100 mL) was added ethyl 2-dimethylaminomethylthiazole-4-carboxylate (8.5 g, 39.7 mmol in 40 mL of tetrahydrofuran) dropwise over 40 min maintaining an internal temperature of 5–10C. The mixture was stirred at this temperature range for 90 min. The reaction was carefully quenched with saturated aqueous ammonium chloride (30 mL). The resulting gray slurry was stirred 15 min and filtered through celite. The pad was well washed with ethyl acetate. The filtrate was washed with brine and dried over sodium sulfate. Concentration of this organic solution gave 4.2 g (62%) of 2-dimethylaminomethyl-4-hydroxymethylthiazole as an amber oil. The material was used without further purification.

$^1$H NMR $\delta$7.12 (s,1 H), 4.71 (s, 2 H), 3.73 (s, 2 H), 2.50 (br s, 1 H), 2.32 (s, 6 H).

A solution of 2-dimethylaminomethyl-4-hydroxymethylthiazole (4.2 g, 27.3 mmol) in methylene chloride (200 mL) was treated with Dess-Martin reagent (14.5 g, 34.1 mmol). The mixture was stirred at ambient temperature for 24 hours. Additional Dess-Martin reagent (2.9 g) was added and the mixture was stirred 4 hours more. The reaction was quenched by addition of saturated aqueous sodium thiosulfate (100 mL) and the pH of the resulting mixture was adjusted to a pH of 10 by addition of solid potassium carbonate. The two phase mixture was filtered. The phases were separated from the filtrate and the aqueous layer was extracted with methylene chloride. The combined organic layers were washed with brine, dried over sodium sulfate, and concentrated to afford a yellow solid. This solid was purified by flash chromatography on silica gel (50×130 mm) eluting first with chloroform (200 mL) and then 2% methanol/chloroform collecting 25 mL fractions. Fractions 51–80 were combined and concentrated to leave 2.9 g of a milky yellow oil. This oil was triturated with 50% ethereal chloroform and a solid was removed by filtration. The filtrate was concentrated to yield 2.6 g (62%) of 2-dimethylaminomethyl-thiazole-4-carboxaldehyde as a yellow oil. This product was used without further purification.

$^1$H NMR $\delta$9.95 (s,1 H), 8.14 (s, 1 H), 3.81 (s, 2 H), 2.36 (s, 6 H).

Separation of Atropisomers

The separation of individual atropisomers from racemic mixtures of compounds of the formula I or from mixtures containing unequal amounts of opposite atropisomers of the formula I can be carried out using HPLC, as exemplified below.

All HPLC analytical separation experimental conditions described below were carried out with a Hewlett Packard model 1050 HPLC. The dimensions of the analytical columns were 4.6 mm×25 cm and the stationary phase particle size was 10 micron. All samples were dissolved in methanol.

EXAMPLE 13

HPLC conditions for separation of atropisomers from Example 1 wherein $R^6$ is 2-fluorophenyl

| Column | Chiralcel OD |
|---|---|
| Mobile Phase | 90/10 hexane/isopropyl alcohol with 0.1% diethylamine |
| Flow Rate | 1 mL/min |
| Detection | UV (250 nM) |
| Retention Time (first atropisomer) | 28.325 min |
| Retention Time (second atropisomer) | 31.808 min |

EXAMPLE 14

HPLC conditions for separation of atropisomers from Example 4 wherein $R^{17}$ is 2-chloropyrid-3-yl and $R^6$ is 2-fluorophenyl

| Column | Chiralcel OD |
|---|---|
| Mobile Phase | 80/20 hexane/isopropyl alcohol with 0.1% diethylamine |
| Flow Rate | 1 mL/min |
| Detection | UV (250 nM) |
| Retention Time (first atropisomer) | 18.679 min |
| Retention Time (second atropisomer) | 22.102 min |

EXAMPLE 15

HPLC conditions for separation of atropisomers from Example 4 wherein $R^{17}$ is 2-methylphenyl and $R^6$ is 2-chlorophenyl

EXAMPLE 16

HPLC conditions for separation of atropisomers form Example 4 wherein $R^{17}$ is 2-chlorophenyl and $R^6$ is 2-methoxyphenyl

| | |
|---|---|
| Column | Chiralpak AD |
| Mobile Phase | 80/20 hexane/isopropyl alcohol with 0.1% diethylamine |
| Flow Rate | 1 mL/min |
| Detection | UV (250 nM) |
| Retention Time (first atropisomer) | 9.162 min |
| Retention Time (second atropisomer) | 17.397 min |

EXAMPLE 17

HPLC conditions for separation of atropisomers form Example 4 wherein $R^{17}$ is 2-methylphenyl and $R^6$ is 2-methyl-1,3-thiazol-4-yl

| | |
|---|---|
| Column | Chiralpak AD |
| Mobile Phase | 80/20 hexane/isopropyl alcohol with 0.1% diethylamine |
| Flow Rate | 1 mL/min |
| Detection | UV (250 nM) |
| Retention Time (first atropisomer) | 10.755 min |
| Retention Time (second atropisomer) | 14.230 min |

EXAMPLE 18

HPLC conditions for separation of atropisomers form Example 4 wherein $R^{17}$ is 2-methylpyrid-3-yl and $R^6$ is 2-methyl-1,3-thiazol-4-yl

| | |
|---|---|
| Column | Chiralcel OD |
| Mobile Phase | 90/10 hexane/isopropyl alcohol with 0.1% diethylamine |
| Flow Rate | 1 mL/min |
| Detection | UV (250 nM) |
| Retention Time (first atropisomer) | 38.038 min |
| Retention Time (second atropisomer) | 45.032 min |

What is claimed is:

1. An atropisomer of the formula

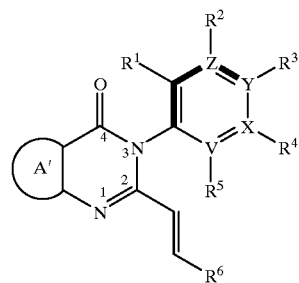

I wherein either each of V, X, Y and Z is carbon or one of them is nitrogen and each of the others is carbon;

each of $R^1$, $R^2$, $R^3$, $R^4$ and $R^5$ is hydrogen, halogen, $(C_1-C_6)$alkyl, trifluoromethyl, cyano, $(C_1-C_6)$alkoxy, $(C_1-C_6)$alkylthio or $-C(=O)-O-(C_1-C_6)$alkyl, with the proviso that: (a) $R^1$ can not be the same as $R^5$ when each of V, X and Z is carbon; (b) at least one of $R^1$ and $R^5$ must be other than hydrogen; and (c) when V, X, Y or Z is nitrogen, then $R^5$, $R^4$, $R^3$ or $R^2$, respectively, is absent;

ring A' is a fused 5 membered heteroaromatic ring which, taken together with the carbon atoms common to both rings of the bicyclic system, has the formula

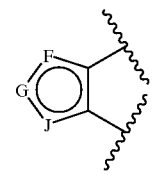

wherein one of the ring atoms "F", "G" and "J" is sulfur and each of the others is carbon;

wherein said fused heteroaromatic ring optionally may be independently substituted on any of the carbon atoms with hydrogen, $(C_1-C_6)$alkyl, halogen, trifluoromethyl, amino-$(CH_2)_n$, $(C_1-C_6)$alkylamino-$(CH_2)_n$—, di$(C_1-C_6)$alkyl-amino-$(CH_2)_n$—, $(C_1-C_6)$alkoxy, hydroxy$(C_1-C_6)$alkyl, $(C_1-C_6)$alkyl-O—$(C_1-C_6)$alkyl-, —CN, $(C_1-C_6)$alkyl-CO—O—$(C_1-C_6)$alkyl-, —$(C_1-C_6)$alkyl-O—CO—O—$(C_1-C_6)$alkyl, $(C_1-C_6)$alkyl-CO—O—, hydroxy, —$NO_2$, $R^{15}$—C(=O)—, $R^{15}$—O—C(=O)—, di$(C_1-C_6)$alkyl-N—C(=O)—, $(C_3-C_7)$cycloalkyl, or $R^{15}$—NH—C(=O)—, or phenyl optionally substituted with halo, $(C_1-C_6)$alkyl, —CN, or —$CF_3$;

$R^6$ is phenyl of the formula $Ph^1$ or a five or six membered heterocycle, wherein said 6-membered heterocycle has the formula

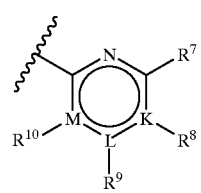

wherein "N" is nitrogen; wherein each of said ring positions "K", "L" and "M" is carbon or nitrogen, with the proviso that only one of "K", "L" or "M" is nitrogen;

wherein said five membered heterocycle has the formula

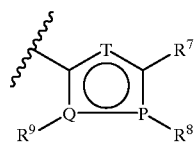

wherein each of said ring positions "P," "Q" and "T" is carbon, nitrogen, oxygen or sulfur; with the proviso that only one of "P," "Q" or "T" can be oxygen or sulfur and at least one of "P," "Q" or "T" must be a heteroatom;

wherein said $Ph^1$ is a group of the formula

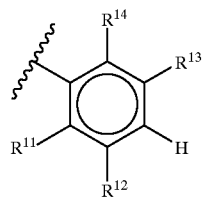

wherein each $R^{15}$ is, independently, hydrogen or $(C_1–C_6)$alkyl;

each of $R^9$, $R^{10}$ and $R^{11}$ is hydrogen, $(C_1–C_6)$alkyl optionally substituted with one to three halogen atoms, halo, $CF_3$, $(C_1–C_6)$alkoxy optionally substituted with one to three halogen atoms, $(C_1–C_6)$alkylthio, $R^{16}O$—$(CH_2)_p$—, $(C_1–C_6)$alkyl-NH—$(CH_2)_p$—, di$(C_1–C_6)$alkyl-N—$(CH_2)_p$—, $(C_3–C_7)$cycloalkyl-NH—$(CH_2)_p$—, $H_2N$—(C=O)—$(CH_2)_p$—, $(C_1–C_6)$alkyl-HN—(C=O)—$(CH_2)_p$—, di$(C_1–C_6)$alkyl-N—(C=O)—$(CH_2)_p$—, $(C_3–C_7)$cycloalkyl-NH—(C=O)—$(CH_2)_p$—, $R^{16}O$—(C=O)—$(CH_2)_p$—, $(C_1–C_6)$alkyl-(O=C)—O—$(C_1–C_6)$alkyl-, $(C_1–C_6)$alkyl-O—(O=C)—O—$(C_1–C_6)$-alkyl-, $(C_1–C_6)$alkyl-(O=C)—O—, $(C_1–C_6)$alkyl-(O=C)—NH—$(CH_2)_p$—, H(O=C)—NH—$(CH_2)_p$—, $(C_1–C_6)$alkyl-(O=C)—N—[$(C_1–C_6)$alkyl]$(CH_2)_p$—, H(O=C)—N—[$(C_1–C_6)$alkyl]$(CH_2)_p$—, hydroxy, H—C(=O)—$(CH_2)_p$—, $(C_1–C_6)$alkyl-C(=O)—, $(C_1–C_6)$alkyl-O—C(=O)—, $R^{15}$—$(CH_2)_p$—O—C(=O)—, amino-$(CH_2)_p$—, hydroxy-$(C_1–C_6)$alkyl-, $(C_1–C_6)$alkyl-O—$(C_1–C_6)$alkyl- or cyano;

each of $R^7$, $R^{12}$ and $R^{13}$ is hydrogen, $(C_1–C_6)$alkyl optionally substituted with one to three halogen atoms, halogen, $CF_3$, $(C_1–C_6)$alkoxy optionally substituted with one to three halogen atoms, $(C_1–C_6)$alkylthio, $R^{16}O$—$(CH_2)_p$—, $(C_1–C_6)$alkyl-NH—$(CH_2)_p$—, di$(C_1–C_6)$alkyl-N—$(CH_2)_p$—, $(C_3–C_7)$cycloalkyl-NH—$(CH_2)_p$—, $H_2N$—(C=O)—$(CH_2)_p$—, $(C_1–C_6)$alkyl-HN—(C=O)—$(CH_2)_p$—, di$(C_1–C_6)$alkyl-N—(C=O)—$(CH_2)_p$—, $(C_3–C_7)$cycloalkyl-NH—(C=O)—$(CH_2)_p$—, $R^{16}O$—(C=O)—$(CH_2)_p$—, $(C_1–C_6)$alkyl-(O=C)—O—$(C_1–C_6)$alkyl-, $(C_1–C_6)$alkyl-O—(O=C)—O—$(C_1–C_6)$-alkyl-, $(C_1–C_6)$alkyl-(O=C)—O—, $(C_1–C_6)$alkyl-(O=C)—NH—$(CH_2)_p$—, H(O=C)—NH—$(CH_2)_p$—, $(C_1–C_6)$alkyl-(O=C)—N—[$(C_1–C_6)$alkyl]$(CH_2)_p$, H(O=C)—N—[$(C_1–C_6)$alkyl]$(CH_2)_p$—, hydroxy, H—C(=O)—$(CH_2)_p$—, $(C_1–C_6)$alkyl-C(=O)—, $(C_1–C_6)$alkyl-O—C(=O)—, $R^{15}$—$(CH_2)_p$—O—C(=O)—, amino-$(CH_2)_p$—, hydroxy-$(C_1–C_6)$alkyl-, $(C_1–C_6)$alkyl-O—$(C_1–C_6)$alkyl-, —CHO or cyano;

each $R^{14}$ is, hydrogen, halogen, cyano or trifluoromethyl, each $R^{16}$ is, hydrogen, $(C_1–C_6)$alkyl, $(C_1–C_6)$alkyl-(C=O)—, $(C_1–C_6)$alkyl-O—(C=O)—, $(C_1–C_6)$alkyl-NH—(C=O)—, or di$(C_1–C_6)$alkyl-N—(C=O)—;

each $R^8$ is hydrogen, cyano, $(C_1–C_6)$alkyl, halogen, trifluoromethyl, —CHO or $(C_1–C_6)$alkoxy;

n is an integer from zero to 3; and p is an integer from zero to 3;

with the proviso that when $R^{11}$ is hydrogen, one of $R^{13}$ and $R^{14}$ is other than hydrogen;

and with the proviso that when "G" is sulfur, $R^6$ is not said 6-membered heterocycle;

or a pharmaceutically-acceptable salt of such an atropisomer.

2. A compound according to claim 1 wherein ring A' is thieno, $R^6$ is 2, 4 or 5-thiazolyl substituted with a methyl group, $R^1$ is methyl, Z is carbon or nitrogen and each of V, X and Y is carbon.

3. A compound according to claim 1 wherein ring A' is thieno, $R^6$ is 2, 4 or 5-thiazolyl substituted with a methyl group, $R^1$ is chloro, Z is nitrogen and each of V, X and Y is carbon.

4. A compound according to claim 1 wherein ring A' is thieno, $R^6$ is phenyl, 2-chlorophenyl, 2-fluorophenyl, 2-bromophenyl or 2-hydroxyphenyl, each of $R^2$, $R^3$, $R^4$ and $R^5$, if present, is hydrogen, and $R^1$ is methyl or chloro.

5. A compound according to claim 1 wherein ring A' is thieno, $R^6$ is 2-pyridyl, each of V, X Y and Z is carbon, each of $R^2$, $R^3$, $R^4$ and $R^5$ is hydrogen, and $R^1$ is chloro.

6. A compound according to claim 1 wherein ring A' is thieno, $R^6$ is 2-fluorophenyl, Z is nitrogen, each of V, X Y and Z is carbon, each of $R^3$, $R^4$ and $R^5$ is hydrogen, and $R^1$ is chloro.

7. A compound according to claim 2, wherein ring A' is thieno and taken together with the pyrimidinone ring forms a 3H-thieno[3,2d]pyrimidin-4-one.

8. A compound according to claim 3, wherein ring A' is thieno and taken together with the pyrimidone ring forms a 3H-thieno[3,2-d]pyrimidin-4-one.

9. A compound according to claim 5, wherein ring A' is thieno and taken together with the pyrimidone ring forms a 3H-thieno[3,2]pyrimidin-4-one.

10. A compound according to claim 4 wherein Z is nitrogen.

11. A compound according to claim 4 wherein Z is carbon and wherein ring A' is thieno and taken together with the pyrimidinone ring forms a 3H-thieno[3,2-d]pyrimidin-4-one.

12. A pharmaceutical composition for treating a disorder or condition, the treatment or prevention of which can be effected or facilitated by reducing or inhibiting glutamate neurotransmission, or for treating stroke, cerebral ischemia, spinal cord trauma, head trauma, Alzheimer's Disease, Huntington's Chorea, amyotrophic lateral sclerosis, AIDS-induced dementia, muscular spasms, migraine headaches, urinary incontinence, psychosis, convulsions, perinatal hypoxia, cardiac arrest, hypoglycemic neuronal damage, opiate tolerance and withdrawal, ocular damage and retinopathy, idiopathic and drug induced Parkinson's Disease, anxiety, emesis, brain edema, chronic or acute pain, tardive dyskinesia or cerebral deficits subsequent to cardiac bypass surgery and grafting, in a mammal, comprising a pharmacologically-effective amount of a compound according to claim 1 and a pharmaceutically acceptable carrier.

13. A method for treating stroke, cerebral ischemia, spinal cord trauma, head trauma, Alzheimer's Disease, Huntington's Chorea, amyotrophic lateral sclerosis, AIDS-induced dementia, muscular spasms, migraine headaches, urinary incontinence, psychosis, convulsions, perinatal hypoxia, cardiac arrest, hypoglycemic neuronal damage, opiate tolerance and withdrawal, ocular damage and retinopathy, idiopathic and drug induced Parkinson's Disease, anxiety, emesis, brain edema, chronic or acute pain, tardive dyskinesia or cerebral deficits subsequent to cardiac bypass surgery and grafting, in a mammal, comprising administering to a mammal requiring such treatment a pharmacologically-effective amount of a compound according to claim 1.

14. A method for treating a disorder or condition, the treatment of which can be effected or facilitated by reducing or inhibiting glutamate neurotransmission in a mammal, comprising administering to a mammal requiring such treatment an amount of a compound according to claim 1 that is effective in treating such disorder or condition.

15. A method for treating stroke, cerebral ischemia, spinal cord trauma, head trauma, Alzheimer's Disease, Huntington's Chorea, amyotrophic lateral sclerosis, AIDS-induced dementia, muscular spasms, migraine headaches, urinary incontinence, psychosis, convulsions, perinatal hypoxia, cardiac arrest, hypoglycemic neuronal damage, opiate tolerance and withdrawal, ocular damage and retinopathy, idiopathic and drug induced Parkinson's Disease, anxiety, emesis, brain edema, chronic or acute pain, tardive dyskinesia or cerebral deficits subsequent to cardiac bypass surgery and grafting, in a mammal, comprising administering to a mammal requiring such treatment a pharmacologically-effective amount of an atropisomer of the formula

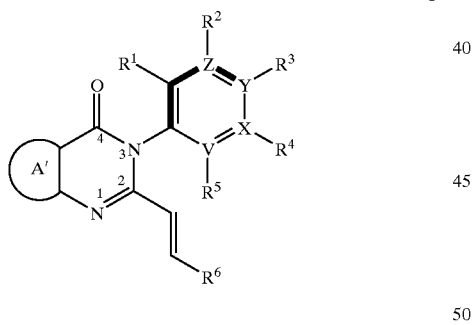

I wherein either each of V, X, Y and Z is carbon or one of them is nitrogen and each of the others is carbon;

each of $R^1$, $R^2$, $R^3$, $R^4$ and $R^5$ is hydrogen, halogen, $(C_1-C_6)$alkyl, trifluoromethyl, cyano, $(C_1-C_6)$alkoxy, $(C_1-C_6)$alkylthio or —C(=O)—O—$(C_1-C_6)$alkyl, with the proviso that: (a) $R^1$ can not be the same as $R^5$ when each of V, X and Z is carbon; (b) at least one of $R^1$ and $R^5$ must be other than hydrogen; and (c) when V, X, Y or Z is nitrogen, then $R^5$, $R^4$, $R^3$ or $R^2$, respectively, is absent;

ring A' is a fused 5 membered heteroaromatic ring which, taken together with the carbon atoms common to both rings of the bicyclic system, has the formula

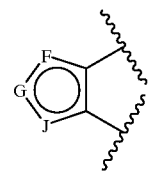

wherein "G" is sulfur and "F" and "J" are carbon;

wherein said fused heteroaromatic ring optionally may be independently substituted on any of the carbon atoms with hydrogen, $(C_1-C_6)$alkyl, halogen, trifluoromethyl, amino-$(CH_2)_n$, $(C_1-C_6)$alkylamino-$(CH_2)_n$—, di$(C_1-C_6)$alkyl-amino-$(CH_2)_n$—, $(C_1-C_6)$alkoxy, hydroxy$(C_1-C_6)$alkyl, $(C_1-C_6)$alkyl-O—$(C_1-C_6)$alkyl-, —CN, $(C_1-C_6)$alkyl-CO—O—$(C_1-C_6)$alkyl-, —$(C_1-C_6)$alkyl-O—CO—O—$(C_1-C_6)$alkyl, $(C_1-C_6)$alkyl-CO—O—, hydroxy, —$NO_2$, $R^{15}$—C(=O)—, $R^{15}$—O—C(=O)—, di$(C_1-C_6)$alkyl-N—C(=O)—, $(C_3-C_7)$cycloalkyl, or $R^{15}$—NH—C(=O)—, or phenyl optionally substituted with halo, $(C_1-C_6)$alkyl, —CN, or —$CF_3$;

$R^6$ is a six membered heterocycle, wherein said 6-membered heterocycle has the formula

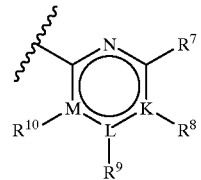

wherein "N" is nitrogen; wherein each of said ring positions "K", "L" and "M" is carbon or nitrogen, with the proviso that only one of "K", "L" or "M" is nitrogen;

wherein each of $R^9$ and $R^{10}$ is hydrogen, $(C_1-C_6)$alkyl optionally substituted with one to three halogen atoms, halo, $CF_3$, $(C_1-C_6)$alkoxy optionally substituted with one to three halogen atoms, $(C_1-C_6)$alkylthio, $R^{16}O$—$(CH_2)_p$—, $(C_1-C_6)$alkyl-NH—$(CH_2)_p$—, di$(C_1-C_6)$alkyl-N—$(CH_2)_p$—, $(C_3-C_7)$cycloalkyl-NH—$(CH_2)_p$—, $H_2N$—(C=O)—$(CH_2)_p$—, $(C_1-C_6)$alkyl-HN—(C=O)—$(CH_2)_p$—, di$(C_1-C_6)$alkyl-N—(C=O)—$(CH_2)_p$—, $(C_3-C_7)$cycloalkyl-NH—(C=O)—$(CH_2)_p$—, $R^{16}O$—(C=O)—$(CH_2)_p$—, $(C_1-C_6)$alkyl-(O=C)—O—$(C_1-C_6)$alkyl-, $(C_1-C_6)$alkyl-(O=C)—O—$(C_1-C_6)$-alkyl-, $(C_1-C_6)$alkyl-(O=C)—O—, $(C_1-C_6)$alkyl-(O=C)—NH—$(CH_2)_p$—, H(O=C)—NH—$(CH_2)_p$—, $(C_1-C_6)$alkyl-(O=C)—N—[$(C_1-C_6)$alkyl]$(CH_2)_p$—, H(O=C)—N—[$(C_1-C_6)$alkyl]$(CH_2)_p$—, hydroxy, H—C(=O)—$(CH_2)_p$—, $(C_1-C_6)$alkyl-C(=O)—, $(C_1-C_6)$alkyl-O—C(=O)—, $R^{15}$—$(CH_2)_p$—O—C(=O)—, amino-$(CH_2)_p$—, hydroxy-$(C_1-C_6)$alkyl-, $(C_1-C_6)$alkyl-O—$(C_1-C_6)$alkyl- or cyano;

$R^7$ is hydrogen, $(C_1-C_6)$alkyl optionally substituted with one to three halogen atoms, halogen, $CF_3$, $(C_1-C_6)$alkoxy optionally substituted with one to three halogen atoms, $(C_1-C_6)$alkylthio, $R^{16}O$—$(CH_2)_p$—, $(C_1-C_6)$alkyl-NH—$(CH_2)_p$—, di$(C_1-C_6)$alkyl-N—$(CH_2)_p$—, $(C_3-C_7)$cycloalkyl-NH—$(CH_2)_p$—, $H_2N$—(C=O)—

$(CH_2)_p$—, $(C_1-C_6)$alkyl-HN—(C=O)—$(CH_2)_p$—, di$(C_1-C_6)$alkyl-N—(C=O)—$(CH_2)_p$—, $(C_3-C_7)$cycloalkyl-NH—(C=O)— $(CH_2)_p$—, $R^{16}O$—(C=O)—$(CH_2)_p$—, $(C_1-C_6)$alkyl-(O=C)—O—$(C_1-C_6)$alkyl-, $(C_{1-6})$alkyl-O—(O=C)—O—$(C_1-C_6)$-alkyl-, $(C_1-C_6)$alkyl-(O=C)—O—, $(C_1-C_6)$alkyl-(O=C)—NH—$(CH_2)_p$—, H(O=C)—NH—$(CH_2)_p$—, $(C_1-C_6)$alkyl-(O=C)—N—[$(C_1-C_6)$alkyl]$(CH_2)_p$—, H(O=C)—N—[$(C_1-C_6)$alkyl]$(CH_2)_p$—, hydroxy, H—C(=O)—$(CH_2)_p$—, $(C_1-C_6)$alkyl-C(=O)—, $(C_1-C_6)$alkyl-O—C(=O)—, $R^{15}$—$(CH_2)_p$—O—C(=O)—, amino-$(CH_2)_p$—, hydroxy-$(C_1-C_6)$alkyl-, $(C_1-C_6)$alkyl-O—$(C_1-C_6)$alkyl-, —CHO or cyano;

each $R^{15}$ is, independently, hydrogen or $(C_1-C_6)$ alkyl;

each $R^{16}$ is, hydrogen, $(C_1-C_6)$alkyl, $(C_1-C_6)$alkyl-(C=O)—, $(C_1-C_6)$alkyl-O—(C=O)—, $(C_1-C_6)$alkyl-NH—(C=O)—, or di$(C_1-C_6)$alkyl-N—(C=O)—;

each $R^8$ is hydrogen, cyano, $(C_1-C_6)$alkyl, halogen, trifluoromethyl, —CHO or $(C_1-C_6)$alkoxy;

n is an integer from zero to 3; and p is an integer from zero to 3;

with the proviso that when $R^{11}$ is hydrogen, one of $R^{13}$ and $R^{14}$ is other than hydrogen;

and with the proviso that when "G" is sulfur, $R^6$ is not said 6-membered heterocycle;

or a pharmaceutically-acceptable salt of such an atropisomer.

16. A method for treating a disorder or condition, the treatment of which can be effected or facilitated by reducing or inhibiting glutamate neurotransmission in a mammal, comprising administering to a mammal requiring such treatment an amount of an atropisomer of the formula

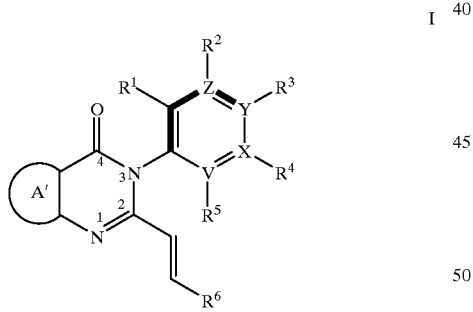

I wherein either each of V, X, Y and Z is carbon or one of them is nitrogen and each of the others is carbon;

each of $R^1$, $R^2$, $R^3$, $R^4$ and $R^5$ is hydrogen, halogen, $(C_1-C_6)$alkyl, trifluoromethyl, cyano, $(C_1-C_6)$alkoxy, $(C_1-C_6)$alkylthio or —C(=O)—O—$(C_1-C_6)$alkyl, with the proviso that: (a) $R^1$ can not be the same as $R^5$ when each of V, X and Z is carbon; (b) at least one of $R^1$ and $R^5$ must be other than hydrogen; and (c) when V, X, Y or Z is nitrogen, then $R^5$, $R^4$, $R^3$ or $R^2$, respectively, is absent;

ring A' is a fused 5 membered heteroaromatic ring which, taken together with the carbon atoms common to both rings of the bicyclic system, has the formula

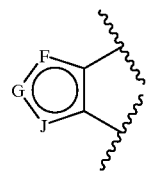

wherein "G" is sulfur and "F" and "J" are carbon;

wherein said fused heteroaromatic ring optionally may be independently substituted on any of the carbon atoms with hydrogen, $(C_1-C_6)$alkyl, halogen, trifluoromethyl, amino-$(CH_2)_n$, $(C_1-C_6)$alkylamino-$(CH_2)_n$—, di$(C_1-C_6)$alkyl-amino-$(CH_2)_n$—, $(C_1-C_6)$alkoxy, hydroxy$(C_1-C_6)$alkyl, $(C_1-C_6)$alkyl-O—$(C_1-C_6)$alkyl-, —CN, $(C_1-C_6)$alkyl-CO—O—$(C_1-C_6)$alkyl-, —$(C_1-C_6)$alkyl-O—CO—O—$(C_1-C_6)$alkyl, $(C_1-C_6)$alkyl-CO—O— hydroxy, —$NO_2$, $R^{15}$—C(=O)—, $R^{15}$—O—C(=O)—, di$(C_1-C_6)$alkyl-N—C(=O)—, $(C_3-C_7)$cycloalkyl, or $R^{15}$—NH—C(=O)—, or phenyl optionally substituted with halo, $(C_1-C_6)$alkyl, —CN, or —$CF_3$;

$R^6$ is a six membered heterocycle, wherein said 6-membered heterocycle has the formula

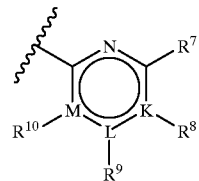

wherein "N" is nitrogen; wherein each of said ring positions "K", "L" and "M" is carbon or nitrogen, with the proviso that only one of "K", "L" or "M" is nitrogen;

wherein each of $R^9$ and $R^{10}$ is hydrogen, $(C_1-C_6)$alkyl optionally substituted with one to three halogen atoms, halo, $CF_3$, $(C_1-C_6)$alkoxy optionally substituted with one to three halogen atoms, $(C_1-C_6)$alkylthio, $R^{16}O$—$(CH_2)_p$—, $(C_1-C_6)$alkyl-NH—$(CH_2)_p$—, di$(C_1-C_6)$alkyl-N—$(CH_2)_p$—, $(C_3-C_7)$cycloalkyl-NH—$(CH_2)_p$—, $H_2N$—(C=O)—$(CH_2)_p$—, $(C_1-C_6)$alkyl-HN—(C=O)—$(CH_2)_p$—, di$(C_1-C_6)$alkyl-N—(C=O)—$(CH_2)_p$—, $(C_3-C_7)$cycloalkyl-NH—(C=O)—$(CH_2)_p$—, $R^{16}O$—(C=O)—$(CH_2)_p$—, $(C_1-C_6)$alkyl-(O=C)—O—$(C_1-C_6)$alkyl-, $(C_1-C_6)$alkyl-O—(O=C)—O—$(C_1-C_6)$-alkyl-, $(C_1-C_6)$alkyl-(O=C)—O—, $(C_1-C_6)$alkyl-(O=C)—NH—$(CH_2)_p$—, H(O=C)—NH—$(CH_2)_p$—, $(C_1-C_6)$alkyl-(O=C)—N—[$(C_1-C_6)$alkyl]$(CH_2)_p$—, H(O=C)—N—[$(C_1-C_6)$alkyl]$(CH_2)_p$—, hydroxy, H—C(=O)—$(CH_2)_p$—, $(C_1-C_6)$alkyl-C(=O)—, $(C_1-C_6)$alkyl-O—C(=O)—, $R^{15}$—$(CH_2)_p$—O—C(=O)—, amino-$(CH_2)_p$—, hydroxy-$(C_1-C_6)$alkyl-, $(C_1-C_6)$alkyl-O—$(C_1-C_6)$alkyl- or cyano;

$R^7$ is hydrogen, $(C_1-C_6)$alkyl optionally substituted with one to three halogen atoms, halogen, $CF_3$, $(C_1-C_6)$alkoxy optionally substituted with one to three halogen atoms, $(C_1-C_6)$alkylthio, $R^{16}O$—$(CH_2)_p$—, $(C_1-C_6)$alkyl-NH—$(CH_2)_p$—, di$(C_1-C_6)$alkyl-N—$(CH_2)_p$—, $(C_3-C_7)$cycloalkyl-NH—$(CH_2)_p$—, $H_2N$—(C=O)—$(CH_2)_p$—, $(C_1-C_6)$alkyl-HN—(C=O)—$(CH_2)_p$—, di($C_1$-$C_6$)alkyl-N—(C=O)—($CH_2$)$_p$—, ($C_3$-$C_7$)cycloalkyl-NH—(C=O)—($CH_2$)$_p$—, $R^{16}$O—(C=O)—($CH_2$)$_p$—, ($C_1$-$C_6$)alkyl-(O=C)—O—($C_1$-$C_6$)alkyl-, ($C_1$-$C_6$)alkyl-O—(O=C)—O—($C_1$-$C_6$)-alkyl-, ($C_1$-$C_6$)alkyl-(O=C)—O—, ($C_1$-$C_6$)alkyl-(O=C)—NH—($CH_2$)$_p$—, H(O=C)—NH—($CH_2$)$_p$—, ($C_1$-$C_6$)alkyl-(O=C)—N—[($C_1$-$C_6$)alkyl]($CH_2$)$_p$—, H(O=C)—N—[($C_1$-$C_6$)alkyl]($CH_2$)$_p$—, hydroxy, H—C(=O)—($CH_2$)$_p$—, ($C_1$-$C_6$)alkyl-C(=O)—, ($C_1$-$C_6$)alkyl-O—C(=O)—, $R^{15}$—($CH_2$)$_p$—O—C(=O )—, amino-($CH_2$)$_p$—, hydroxy-($C_1$-$C_6$)alkyl-, ($C_1$-$C_6$)alkyl-O—($C_1$-$C_6$)alkyl-, —CHO or cyano;

each $R^{15}$ is, independently, hydrogen or ($C_1$-$C_6$)alkyl;

each $R^{16}$ is, hydrogen, ($C_1$-$C_6$)alkyl, ($C_1$-$C_6$)alkyl-(C=O)—, ($C_1$-$C_6$)alkyl-O—(C=O)—, ($C_1$-$C_6$)alkyl-NH—(C=O)—, or di($C_1$-$C_6$)alkyl-N—(C=O)—;

each $R^8$ is hydrogen, cyano, ($C_1$-$C_6$)alkyl, halogen, trifluoromethyl, —CHO or ($C_1$-$C_6$)alkoxy;

n is an integer from zero to 3; and p is an integer from zero to 3;

with the proviso that when $R^{11}$ is hydrogen, one of $R^{13}$ and $R^{14}$ is other than hydrogen;

and with the proviso that when "G" is sulfur, $R^6$ is not said 6-membered heterocycle;

or a pharmaceutically-acceptable salt of such an atropisomer.

* * * * *